(12) United States Patent
Gielen-Haertwig et al.

US008097629B2

(10) Patent No.: US 8,097,629 B2
(45) Date of Patent: *Jan. 17, 2012

(54) DIHYDROPYRIDINONE DERIVATIVES

(75) Inventors: Heike Gielen-Haertwig, Monheim (DE); Barbara Albrecht, Wülfrath (DE); Marcus Bauser, Wuppertal (DE); Jörg Keldenich, Wuppertal (DE); Volkhart Li, Velbert (DE); Josef Pernerstorfer, Hofheim (DE); Karl-Heinz Schlemmer, Wuppertal (DE); Leila Telan, Düsseldorf (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 834 days.

This patent is subject to a terminal disclaimer.

(21) Appl. No.: 10/589,907

(22) PCT Filed: Feb. 5, 2005

(86) PCT No.: PCT/EP2005/001192
§ 371 (c)(1),
(2), (4) Date: Jun. 29, 2007

(87) PCT Pub. No.: WO2005/080372
PCT Pub. Date: Sep. 1, 2005

(65) Prior Publication Data
US 2008/0045541 A1   Feb. 21, 2008

(30) Foreign Application Priority Data
Feb. 19, 2004 (EP) .................................... 04003741

(51) Int. Cl.
*C07D 211/76* (2006.01)
*C07D 401/06* (2006.01)
*C07D 405/12* (2006.01)
*C07D 409/12* (2006.01)
*C07D 413/12* (2006.01)
*A61K 31/4422* (2006.01)
*A61K 31/4427* (2006.01)
*A61K 31/443* (2006.01)
*A61K 31/4436* (2006.01)
*A61K 31/4545* (2006.01)
*A61K 31/496* (2006.01)

(52) U.S. Cl. ........... 514/253.11; 514/235.8; 514/253.12; 514/316; 514/318; 514/336; 514/350; 540/575; 540/597; 544/60; 544/121; 544/349; 544/364; 544/365; 546/187; 546/194; 546/261; 546/268.1; 546/283.4; 546/299

(58) Field of Classification Search ........................ None
See application file for complete search history.

(56) References Cited

U.S. PATENT DOCUMENTS

| 5,532,366 | A | 7/1996 | Edwards et al. |
|---|---|---|---|
| 7,199,136 | B2 | 4/2007 | Gielen-Haertwig et al. |
| 7,230,017 | B2 * | 6/2007 | Gielen-Haertwig et al. . 514/350 |
| 7,687,510 | B2 | 3/2010 | Gielen-Haertwig et al. |
| 7,893,073 | B2 | 2/2011 | Gielen-Haertwig et al. |
| 2008/0045541 | A1 | 2/2008 | Gielen-Haertwig et al. |
| 2008/0064704 | A1 * | 3/2008 | Gielen-Haertwig et al. ........ 514/252.14 |
| 2010/0184788 | A1 | 7/2010 | Gielen-Haretwig et al. |

FOREIGN PATENT DOCUMENTS

| EP | 0002231 | 6/1979 |
|---|---|---|
| GB | 2383326 | 6/2003 |
| WO | 2004020410 | 3/2004 |
| WO | 2004020412 | 3/2004 |
| WO | 2005037799 A1 | 4/2005 |
| WO | 2005082864 A2 | 9/2005 |

OTHER PUBLICATIONS

Vippagunta et al. Advanced Drug Delivery Reviews, vol. 48, pp. 3-26 (2001).*
R.A. Stockley, Neutrophils and Protease/Antiprotease Imbalance, Am. J. Respir. Crit. Care Med., 160:S49-S52 (1999).
Tiefenbacher, et al., Inhibition of elastase improves myocardial function after repetitive ischaemia and myocardial infarction in the rat heart, Eur. J. Physiol., 433:563-570 (1997).
Dinerman, et al., Increased Neutrophil Elastase Release in Unstable Angina Pectoris and Acute Myocardial Infarction, J, Am. Coll. Cardiol. 15(7):1559-1563 (1990).
Gilbert, et al., Increased expression of promatrix metalloproteinase-9 and neutrophil elastase in canine dilated cardiomyopathy, Cardiov. Res., 34:377-383 (1997).
Dollery, et al., Neutrophil Elastase in Human Atherosclerotic Plaques: Production by Macrophages, Circulation, 107:2829-2836 (2003).
Erian, et al., A novel Synthesis of fused pyrazole systems as antimicrobial agents, Pharmazie, 53:748-751 (1998).
Namazi, et al., "Investigation the Chemical Reactivity of Positions N-3, C-5 and C6-Methyl Group in Biginelli Type Compounds and Synthesis of new Dihydropyrimidine Derivatives," J. Heterocyclic Chem., 38: 1051-1054 (2001).
Ohmoto, et al., "Development of Orally Active Nonpeptiidic Inhibitors of Human Neutrophil Elastase;" J. Med. Chem. 44 pp. 1268-1285 (2001).
Palomo et al. "Preparation of 3-Alkyl beta-Lactams via the Ketene-Imine Cycloaddition Reaction Using alpha-(Phenylthio)alkanoyl Halides as Starting Materials: Application to the Sysnthesis of (+/−)-Carbapenem Building Blocks and Related Compounds," J. Org. Chem. 56:4418-4428 (1991).

(Continued)

*Primary Examiner* — Emily Bernhardt
(74) *Attorney, Agent, or Firm* — Karen B. King; Thomas C. Blankinship

(57) ABSTRACT

The invention relates to novel dihydropyridinone derivatives, processes for their preparation, and their use in medicaments, especially for the treatment of chronic obstructive pulmonary diseases, acute coronary syndrome, acute myocardial infarction and heart failure development.

4 Claims, No Drawings

OTHER PUBLICATIONS

Walker et al. "Strategies for the Inhibition of Serine Proteases," CMLS, Cell. Mol. Life Sci. 58: 596-624 (2001).

Abbenante et al. "Protease Inhibitors in the Clinic," Medicinal Chemistry, 1:71-104 (2005).

Chughtai et al. "Potential Role of Inhibitors of Neutrophil Elastase in Treateing Diseases of the Airway," Journal of Aerosol Medicine, 17(4): 289-298 (2004).

Ulrich, Chapter 4: Crystallization, Kirk-Othmer Encyclopeida of Chemical Technology, Aug. 2002, (7 pages provided).

Roghanian, et al., "Inflammatory Lung Secretions Inhibit Dendritic Cell Maturation and Function via Neutrophil Elastase," Am. J. of Respiratory and Critical Care Medicine, 174:1189-1109 (2006).

Hsieh, et al., "The evaluation and structure-activity relationships of 2-benzolaminobenzoic esters and their analogues as anti-inflammatory and anti-platelet aggregation agents," Bioorganic & Med. Chem. Lett., 17:1812-1817 (2007).

Kyne, et al., "The evaluation of structure-activity relationships of 2-benzoylamino benzoic esters and their analogues as anti-inflammatory and anti-platelet aggregation agents," Am. Heart J., 139(1): 94-100, (2000).

Lewandowski, et al., "A combinatorial approach to recognition of chirality: preparation of highly enantioselective aryl-dihydropyrimidine selectors for chiral HPLC," J. Comb. Chem., 1:105-112 (1999).

Pending U.S. Appl. No. 10/590,770, filed Jun. 18, 2007. Published as US2008-0064704.

Pending U.S. Appl. No. 12/633,723, filed Dec. 8, 2009. Published as US2010-0814788.

* cited by examiner

DIHYDROPYRIDINONE DERIVATIVES

The present invention relates to novel dihydropyridinone derivatives, processes for their preparation, and their use in medicaments, especially for the treatment of chronic obstructive pulmonary diseases, acute coronary syndrome, acute myocardial infarction and heart failure development.

The fibrous protein elastin, which comprises an appreciable percentage of all protein content in some tissues, such as the arteries, some ligaments, the lungs and the heart, can be hydrolysed or otherwise destroyed by a select group of enzymes classified as elastases. Human leukocyte elastase (HLE, EC 3.4.21.37), also known as human neutrophil elastase (HNE), is a glycosylated, strongly basic serine protease and is found in the azurophilic granules of human polymorphonuclear leukocytes (PMN). HNE is released from activated PMN and has been implicated causally in the pathogenesis of acute and chronic inflammatory diseases. HNE is capable of degrading a wide range of matrix proteins including elastin and collagen, and in addition to these actions on connective tissue HNE has a broad range of inflammatory actions including upregulation of IL-8 gene expression, oedema formation, mucus gland hyperplasia and mucus hypersecretion. It also acts as a mediator of tissue injury by hydrolysing collagen structures, e.g. in the heart after acute myocardial infarction or during the development of heart failure, thus damaging endothelial cells, promoting extravasation of neutrophils adhering to the endothelium and influencing the adhesion process itself.

Pulmonary diseases where HNE is believed to play a role include lung fibrosis, pneumonia, acute respiratory distress syndrome (ARDS), pulmonary emphysema, including smoking-induced emphysema, chronic obstructive pulmonary diseases (COPD) and cystic fibrosis. In cardiovascular diseases, HNE is involved in the enhanced generation of ischaemic tissue injury followed by myocardial dysfunction after acute myocardial infarction and in the remodelling processes occurring during the development of heart failure. HNE has also been causally implicated in rheumatoid arthritis, atherosclerosis, brain trauma, cancer and related conditions in which neutrophil participation is involved.

Thus, inhibitors of HLE activity can be potentially useful in the treatment of a number of inflammatory diseases, especially of chronic obstructive pulmonary diseases [R. A. Stockley, *Neutrophils and protease/antiprotease imbalance*, Am. J. Respir. Crit. Care 160, S49-S52 (1999)]. Inhibitors of HLE activity can also be potentially useful in the treatment of acute myocardial syndrome, unstable angina pectoris, acute myocardial infarction and coronary artery bypass grafts (CABG) [C. P. Tiefenbacher et al., *Inhibition of elastase improves myocardial function after repetitive ischaemia and myocardial infarction in the rat heart*, Eur. J. Physiol. 433, S563-S570 (1997); Dinerman et al., *Increased neutrophil elastase release in unstable angina pectoris and acute myocardial infarction*, J. Am. Coll. Cardiol. 15, 1559-1563 (1990)], of the development of heart failure [S. J. Gilbert et al., *Increased expression of promatrix metalloproteinase-9 and neutrophil elastase in canine dilated cardiomyopathy*, Cardiov. Res. 34, S377-S383 (1997)] and of atherosclerosis [Dollery et al., *Neutrophil elastase in human atherosclerotic plaque*, Circulation 107, 2829-2836 (2003)].

Ethyl 6-amino-1,4-bis(4-chlorophenyl)-5-cyano-2-methyl-1,4-dihydro-3-pyridinecarboxylate has been synthesized and tested for potential antimicrobial activity as described in A. W. Erian et al., *Pharmazie* 53 (11), 748-751 (1998).

The present invention relates to compounds of the general formula (I)

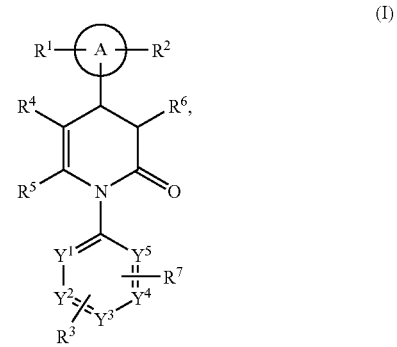

wherein

A represents an aryl or heteroaryl ring, $R^1$, $R^2$ and $R^3$ independently from each other represent hydrogen, halogen, nitro, cyano, trifluoromethyl, $C_1$-$C_6$-alkyl, hydroxy, $C_1$-$C_6$-alkoxy or trifluoromethoxy, wherein $C_1$-$C_6$-alkyl and $C_1$-$C_6$-alkoxy can be further substituted with one to three identical or different radicals selected from the group consisting of hydroxy and $C_1$-$C_4$-alkoxy, $R^4$ represents $C_1$-$C_6$-alkylcarbonyl, $C_1$-$C_6$-alkoxycarbonyl, $C_2$-$C_6$-alkenoxycarbonyl, hydroxycarbonyl, aminocarbonyl, mono- or di-$C_1$-$C_6$-alkylaminocarbonyl, $C_3$-$C_8$-cycloalkylaminocarbonyl, N-(heterocyclyl)-aminocarbonyl or cyano, wherein $C_1$-$C_6$-alkylcarbonyl, $C_1$-$C_6$-alkoxycarbonyl, mono- and di-$C_1$-$C_6$-alkylaminocarbonyl can be substituted with one to three identical or different radicals selected from the group consisting of hydroxy, $C_1$-$C_4$-alkoxy, hydroxycarbonyl, $C_1$-$C_4$-alkoxycarbonyl, amino, mono- and di-$C_1$-$C_4$-alkylamino, aminocarbonyl, mono- and di-$C_1$-$C_4$-alkylaminocarbonyl, $C_1$-$C_4$-alkylcarbonylamino, phenyl, heteroaryl and heterocyclyl, and wherein phenyl can be further substituted with halogen and wherein N-(heterocyclyl)-aminocarbonyl can be further substituted with $C_1$-$C_4$-alkyl or benzyl, $R^5$ represents $C_1$-$C_4$-alkyl, $R^6$ represents a group of the formula

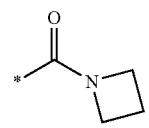

which can be substituted by up to two radicals independently selected from the group consisting of $C_1$-$C_6$-alkyl, $C_1$-$C_6$-alkoxy, hydroxycarbonyl, $C_1$-$C_6$-alkoxycarbonyl and phenoxy which for its part can be further substituted by halogen or trifluoromethyl, a group of the formula

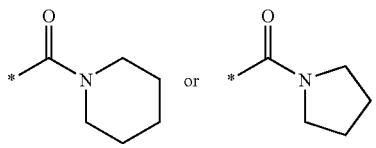 or 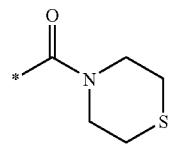

which are substituted by one or two radicals independently selected from the group consisting of $C_1$-$C_6$-alkyl, hydroxy, $C_1$-$C_6$-alkoxy, hydroxycarbonyl, $C_1$-$C_6$-alkoxycarbonyl, $C_1$-$C_6$-alkoxycarbonylamino, oxo, N—$C_1$-$C_6$-alkylimino, N—$C_1$-$C_6$-alkoxyimino, benzyl and 5- to 6-membered heterocyclyl which for its part can be further substituted by $C_1$-$C_4$-alkyl, a group of the formula

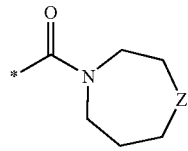

wherein Z represents $CH_2$ or N—$R^{6A}$, wherein $R^{6A}$ represents hydrogen, $C_1$-$C_6$-alkyl, $C_1$-$C_6$-alkylcarbonyl or $C_1$-$C_6$-alkoxycarbonyl, a group of the formula

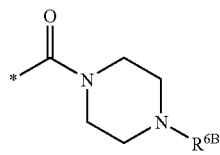

wherein $R^{6B}$ is selected from the group consisting of phenyl or 5- to 6-membered heteroaryl each of which can be further substituted by up to three radicals independently selected from the group consisting of halogen, trifluoromethyl, nitro, cyano, $C_1$-$C_6$-alkyl, hydroxycarbonyl, $C_1$-$C_6$-alkoxycarbonyl and $C_1$-$C_6$-alkylcarbonyl, $C_3$-$C_8$-cycloalkyl $C_1$-$C_6$-alkyl which is substituted by hydroxy, $C_1$-$C_6$-alkoxy, di-$C_1$-$C_6$-alkylamino, hydroxycarbonyl, $C_1$-$C_6$-alkoxycarbonyl, 5- to 6-membered heterocyclyl or by 5- to 6-membered heteroaryl or phenyl which for their part can be further substituted by up to three radicals independently selected from the group consisting of $C_1$-$C_4$-alkyl, halogen and hydroxycarbonyl, 5- to 6-membered heteroarylcarbonyl and $C_1$-$C_6$-alkoxycarbonyl, a group of the formula

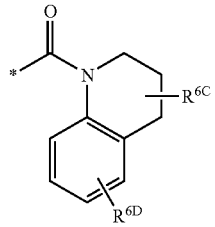

a group of the formula

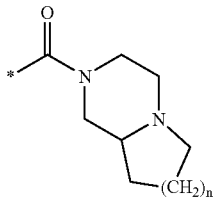

wherein $R^{6C}$ represents hydrogen or $C_1$-$C_4$-alkyl, and $R^{6D}$ represents hydrogen or halogen, a group of the formula

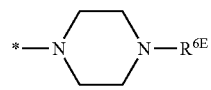

wherein n represents an integer of 1 or 2, mono- or di-$C_1$-$C_6$-alkylaminocarbonyl wherein the alkyl moiety or at least one alkyl moiety, respectively, is substituted by phenyl or 5- to 6-membered heteroaryl each of which are further substituted by one, two or three radicals independently selected from the group consisting of halogen, nitro, cyano, trifluoromethyl, $C_1$-$C_4$-alkyl, hydroxy, $C_1$-$C_4$-alkoxy, trifluoromethoxy, di-$C_1$-$C_4$-alkylamino, hydroxycarbonyl and $C_1$-$C_4$-alkoxycarbonyl, $C_1$-$C_6$-alkoxy which is further substituted by hydroxy, $C_1$-$C_4$-alkoxy, di-$C_1$-$C_4$-alkylamino, $C_1$-$C_4$-alkoxycarbonyl or hydroxycarbonyl, phenoxy N—$C_1$-$C_4$-alkyl-N-phenylamino $C_3$-$C_8$-cycloalkyl cyano or by a group of the formula

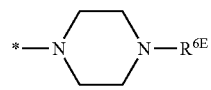

wherein $R^{6E}$ represents $C_1$-$C_6$-alkyl, $C_1$-$C_6$-alkylcarbonyl, $C_1$-$C_6$-alkoxycarbonyl or phenyl which for its part can be further substituted by halogen, $C_1$-$C_4$-alkyl or $C_1$-$C_4$-alkoxy, N—C$_1$-C$_6$-alkyl-N—C$_3$-C8-cycloalkylaminocarbonyl wherein the alkyl moiety can be further substituted by phenyl, 5- to 6-membered heteroaryl, hydroxycarbonyl or C$_1$-C$_6$-alkoxycarbonyl, arylaminocarbonyl wherein the aryl moiety is further substituted by one, two or three radicals independently selected from the group consisting of trifluoromethyl and C$_1$-C$_4$-alkyl, N—C$_1$-C$_6$-alkyl-N-arylaminocarbonyl wherein the aryl moiety is substituted by one, two or three radicals independently selected from the group consisting of C$_1$-C$_4$-alkyl and halogen, and/or wherein the alkyl moiety is substituted by phenyl, or a group of the formula

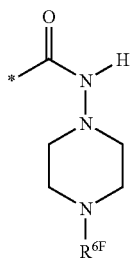

wherein R$^{6F}$ represents hydrogen hydrogen, C$_1$-C$_6$-alkyl, C$_1$-C$_6$-alkylcarbonyl or C$_1$-C$_6$-alkoxycarbonyl, R$^7$ represents hydrogen, halogen, nitro, cyano, trifluoromethyl, C$_1$-C$_6$-alkyl, hydroxy, C$_1$-C$_6$-alkoxy or trifluoromethoxy, wherein C$_1$-C$_6$-alkyl and C$_1$-C$_6$-alkoxy can be further substituted with one to three identical or different radicals selected from the group consisting of hydroxy and C$_1$-C$_4$-alkoxy, and Y$^1$, Y$^2$, Y$^3$, Y$^4$ and Y$^5$ independently from each other represent CH or N, wherein the ring contains either 0, 1 or 2 nitrogen atoms.

The compounds according to this invention can also be present in the form of their salts, hydrates and/or solvates.

Physiologically acceptable salts are preferred in the context of the present invention.

Physiologically acceptable salts according to the invention are non-toxic salts which in general are accessible by reaction of the compounds (I) with an inorganic or organic base or acid conventionally used for this purpose. Non-limiting examples of pharmaceutically acceptable salts of compounds (I) include the alkali metal salts, e.g. lithium, potassium and sodium salts, the alkaline earth metal salts such as magnesium and calcium salts, the quaternary ammonium salts such as, for example, triethyl ammonium salts, acetates, benzene sulphonates, benzoates, dicarbonates, disulphates, ditartrates, borates, bromides, carbonates, chlorides, citrates, dihydrochlorides, fumarates, gluconates, glutamates, hexyl resorcinates, hydrobromides, hydrochlorides, hydroxynaphthoates, iodides, isothionates, lactates, laurates, malates, maleates, mandelates, mesylates, methylbromides, methylnitrates, methylsulphates, nitrates, oleates, oxalates, palmitates, pantothenates, phosphates, diphosphates, polygalacturonates, salicylates, stearates, sulphates, succinates, tartrates, tosylates, valerates, and other salts used for medicinal purposes.

Hydrates of the compounds of the invention or their salts are stoichiometric compositions of the compounds with water, such as for example hemi-, mono-, or dihydrates.

Solvates of the compounds of the invention or their salts are stoichiometric compositions of the compounds with solvents.

The present invention includes both the individual enantiomers or diastereomers and the corresponding racemates or diastereomeric mixtures of the compounds according to the invention and their respective salts. In addition, all possible tautomeric forms of the compounds described above are included according to the present invention. The diastereomeric mixtures can be separated into the individual isomers by chromatographic processes. The racemates can be resolved into the respective enantiomers either by chromatographic processes on chiral phases or by resolution.

In the context of the present invention, the substituents, if not stated otherwise, in general have the following meaning:

Alkyl in general represents a straight-chain or branched hydrocarbon radical having 1 to 6, preferably 1 to 4 carbon atoms. Non-limiting examples include methyl, ethyl, n-propyl, isopropyl, n-butyl, isobutyl, sec.-butyl, tert.-butyl, pentyl, isopentyl, hexyl, isohexyl. The same applies to radicals such as alkoxy, alkylamino, alkoxycarbonyl and alkoxycarbonylamino.

Alkoxy illustratively and preferably represents methoxy, ethoxy, n-propoxy, isopropoxy, tert.-butoxy, n-pentoxy and n-hexoxy.

Alkenoxy illustratively and preferably represents allyloxy, but-2-en-1-oxy, pent-3-en-1-oxy and hex-2-en-1-oxy.

Alkylcarbonyl in general represents a straight-chain or branched hydrocarbon radical having 1 to 6, preferably 1 to 4 carbon atoms which has a carbonyl function at the position of attachment. Non-limiting examples include formyl, acetyl, n-propionyl, n-butyryl, isobutyryl, pivaloyl, n-hexanoyl.

Alkylcarbonylamino in general represents a straight-chain or branched hydrocarbon radical having 1 to 6, preferably 1 to 4 carbon atoms which has a carbonylamino (—CO—NH—) function at the position of attachment and which is bonded to the carbonyl group. Non-limiting examples include formylamino, acetylamino, n-propionylamino, n-butyrylamino, isobutyrylamino, pivaloylamino, n-hexanoylamino.

Alkoxycarbonyl illustratively and preferably represents methoxycarbonyl, ethoxycarbonyl, n-propoxycarbonyl, isopropoxycarbonyl, tert.-butoxycarbonyl, n-pentoxycarbonyl and n-hexoxycarbonyl.

Alkenoxycarbonyl illustratively and preferably represents allyloxycarbonyl, but-2-en-1-oxycarbonyl, pent-3-en-1-oxycarbonyl and hex-2-en-1-oxycarbonyl.

Alkylamino represents an alkylamino radical having one or two (independently selected) alkyl substituents, illustratively and preferably representing methylamino, ethylamino, n-propylamino, isopropylamino, tert.-butylamino, n-pentylamino, n-hexylamino, N,N-dimethylamino, N,N-diethylamino, N-ethyl-N-methylamino, N-methyl-N-n-propylamino, N-isopropyl-N-n-propylamino, N-tert.-butyl-N-methylamino, N-ethyl-N-n-pentylamino and N-n-hexyl-N-methylamino.

Alkylaminocarbonyl represents an alkylaminocarbonyl radical having one or two (independently selected) alkyl substituents, illustratively and preferably representing methylaminocarbonyl, ethylaminocarbonyl, n-propylaminocarbonyl, isopropylaminocarbonyl, tert-butylaminocarbonyl, n-pentylaminocarbonyl, n-hexylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl, N-tert.-butyl-N-methylaminocarbonyl, N-ethyl-N-n-pentylaminocarbonyl and N-n-hexyl-N-methylaminocarbonyl.

Alkylsulfonyloxy in general represents a straight-chain or branched hydrocarbon radical having 1 to 4, preferably 1 to 3 carbon atoms which has a sulfonyloxy (—SO₂—O—) function at the position of attachment and which is bonded to the sulfonyl group. Non-limiting examples include methylsulfonyloxy, ethylsulfonyloxy, n-propylsulfonyloxy, isopropylsulfonyloxy, n-butylsulfonyloxy, tert.-butylsulfonyloxy.

Cycloalkyl in general represents a cyclic saturated hydrocarbon radical having 3 to 8, preferably 3 to 6 carbon atoms. Non-limiting examples include cyclopropyl, cyclobutyl, cyclopentyl, cyclohexyl and cycloheptyl.

Cycloalkylaminocarbonyl represents a cycloalkylaminocarbonyl radical having one or two (independently selected) cycloalkyl substituents with 3 to 8, preferably 4 to 6 ring carbon atoms which is bound via a carbonyl group, illustratively and preferably representing cyclopropylaminocarbonyl, cyclobutylaminocarbonyl, cyclopentylaminocarbonyl, cyclohexylaminocarbonyl and cycloheptylaminocarbonyl.

Aryl per se and in arylcarbonyl, aryloxycarbonyl or arylaminocarbonyl represents a mono- to tricyclic aromatic carbocyclic radical having generally 6 to 14 carbon atoms, illustratively and preferably representing phenyl, naphthyl and phenanthrenyl.

Arylcarbonyl illustratively and preferably represents benzoyl and naphthoyl.

Aryloxycarbonyl illustratively and preferably represents phenoxycarbonyl and naphthoxycarbonyl.

Arylaminocarbonyl illustratively and preferably represents phenylaminocarbonyl and naphthylaminocarbonyl.

Heteroaryl represents an aromatic mono- or bicyclic radical having generally 5 to 10 and preferably 5 or 6 ring atoms and up to 5 and preferably up to 4 hetero atoms selected from the group consisting of S, O and N, illustratively and preferably representing thienyl, furyl, pyrrolyl, thiazolyl, oxazolyl, imidazolyl, pyridyl, pyrimidyl, pyridazinyl, indolyl, indazolyl, benzofuranyl, benzothiophenyl, quinolinyl, isoquinolinyl.

Heterocyclyl per se and in heterocyclylcarbonyl represents a mono- or polycyclic, preferably mono- or bicyclic, nonaromatic heterocyclic radical having generally 4 to 10 and preferably 5 to 8 ring atoms and up to 3 and preferably up to 2 heteroatoms and/or hetero groups selected from the group consisting of N, O, S, SO and SO₂. The heterocyclyl radicals can be saturated or partially unsaturated. Preference is given to 5- to 8-membered monocyclic saturated heterocyclyl radicals having up to two heteroatoms selected from the group consisting of O, N and S, such as illustratively and preferably tetrahydrofuran-2-yl, pyrrolin-1-yl, pyrrolidin-2-yl, pyrrolidin-3-yl, pyrrolinyl, piperidinyl, morpholinyl, thiomorpholinyl, perhydroazepinyl.

Heterocyclylcarbonyl illustratively and preferably represents tetrahydrofuran-2-carbonyl, pyrrolidine-1-carbonyl, pyrrolidine-2-carbonyl, pyrrolidine-3-carbonyl, pyrrolinecarbonyl, piperidinecarbonyl, morpholinecarbonyl, perhydroazepinecarbonyl.

Halogen represents fluorine, chlorine, bromine and iodine.

When stated, that $Y^1, Y^2, Y^3, Y^4$ and $Y^5$ represent CH or N, CH shall also stand for a ring carbon atom, which is substituted with a substituent $R^3$ or $R^7$.

A * symbol next to a bond denotes the point of attachment in the molecule.

In another preferred embodiment, the present invention relates to compounds of general formula (I), wherein A represents an aryl or heteroaryl ring, $R^1, R^2$ and $R^3$ independently from each other represent hydrogen, halogen, nitro, cyano, trifluoromethyl, $C_1$-$C_6$-alkyl, hydroxy, $C_1$-$C_6$-alkoxy or trifluoromethoxy, wherein $C_1$-$C_6$-alkyl and $C_1$-$C_6$-alkoxy can be further substituted with one to three identical or different radicals selected from the group consisting of hydroxy and $C_1$-$C_4$-alkoxy, $R^4$ represents $C_1$-$C_6$-alkylcarbonyl, $C_1$-$C_6$-alkoxycarbonyl, hydroxycarbonyl, aminocarbonyl, mono- or di-$C_1$-$C_4$-alkylaminocarbonyl or cyano, wherein $C_1$-$C_6$-alkylcarbonyl, $C_1$-$C_6$-alkoxycarbonyl, mono- and di-$C_1$-$C_4$-alkylaminocarbonyl can be substituted with one to three identical or different radicals selected from the group consisting of hydroxy, $C_1$-$C_4$-alkoxy, hydroxycarbonyl, $C_1$-$C_4$-alkoxycarbonyl, amino, mono- and di-$C_1$-$C_4$-alkylamino, aminocarbonyl, mono- and di-$C_1$-$C_4$-alkylaminocarbonyl, $C_1$-$C_4$-alkylcarbonylamino and heteroaryl, $R^5$ represents $C_1$-$C_4$-alkyl, $R^6$ represents a group of the formula

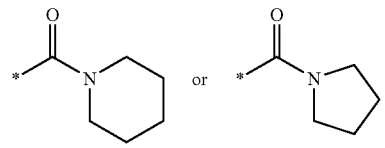

which are substituted by one or two radicals independently selected from the group consisting of $C_1$-$C_6$-alkyl, hydroxy, $C_1$-$C_6$-alkoxy, hydroxycarbonyl, $C_1$-$C_6$-alkoxycarbonyl, $C_1$-$C_6$-alkoxycarbonylamino, oxo, pyrrolidino, piperidino and morpholino, a group of the formula

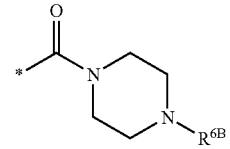

wherein $R^{6B}$ is selected from the group consisting of phenyl or pyridyl each of which can be further substituted by up to three radicals independently selected from the group consisting of halogen, trifluoromethyl, nitro, cyano, $C_1$-$C_6$-alkyl, hydroxycarbonyl, $C_1$-$C_6$-alkoxycarbonyl and $C_1$-$C_6$-alkylcarbonyl, $C_1$-$C_6$-alkyl which is substituted by hydroxy, $C_1$-$C_6$-alkoxy, di-$C_1$-$C_6$-alkylamino, hydroxycarbonyl, $C_1$-$C_6$-alkoxycarbonyl, 5- to 6-membered heterocyclyl or by 5- to 6-membered heteroaryl or phenyl which for their part can be further substituted by up to three radicals independently selected from the group consisting of $C_1$-$C_4$-alkyl, halogen and hydroxycarbonyl, and $C_1$-$C_6$-alkoxycarbonyl, mono- or di-$C_1$-$C_6$-alkylaminocarbonyl wherein the alkyl moiety or at least one alkyl moiety, respectively, is substituted by phenyl or 5- to 6-membered heteroaryl each of which are further substituted by one, two or three radicals independently selected from the group consisting of halogen, nitro, cyano, trifluoromethyl, $C_1$-$C_4$-alkyl, hydroxy, $C_1$-$C_4$-alkoxy, trifluoromethoxy, di-$C_1$-$C_4$-alkylamino, hydroxycarbonyl and $C_1$-$C_4$-alkoxycarbonyl, $C_1$-$C_6$-alkoxy which is further substituted by hydroxy, $C_1$-$C_4$-alkoxy, di-$C_1$-$C_4$-alkylamino, $C_1$-$C_4$-alkoxycarbonyl or hydroxycarbonyl, or by a group of the formula

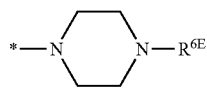

wherein $R^{6E}$ represents $C_1$-$C_6$-alkyl, $C_1$-$C_6$-alkylcarbonyl, $C_1$-$C_6$-alkoxycarbonyl or phenyl which for its part can be further substituted by halogen, $C_1$-$C_4$-alkyl or $C_1$-$C_4$-alkoxy, or N—$C_1$-$C_6$-alkyl-N—$C_3$-$C_8$-cycloalkylaminocarbonyl wherein the alkyl moiety can be further substituted by phenyl, 5- to 6-membered heteroaryl, hydroxycarbonyl or $C_1$-$C_6$-alkoxycarbonyl, $R^7$ represents hydrogen, halogen, nitro, cyano, trifluoromethyl, $C_1$-$C_6$-alkyl, hydroxy, $C_1$-$C_6$-alkoxy or trifluoromethoxy, wherein $C_1$-$C_6$-alkyl and $C_1$-$C_6$-alkoxy can be further substituted with one to three identical or different radicals selected from the group consisting of hydroxy and $C_1$-$C_4$-alkoxy, and $Y^1, Y^2, Y^3, Y^4$ and $Y^5$ independently from each other represent CH or N, wherein the ring contains either 0, 1 or 2 nitrogen atoms.

In another particular preferred embodiment, the present invention relates to compounds of general formula (I), wherein A represents a phenyl or pyridyl ring, $R^1, R^2$ and $R^3$ independently from each other represent hydrogen, fluoro, chloro, bromo, nitro, cyano, methyl, ethyl, trifluoromethyl or trifluoromethoxy, $R^4$ represents $C_1$-$C_6$-alkylcarbonyl, $C_1$-$C_6$-alkoxycarbonyl or cyano, wherein $C_1$-$C_6$-alkylcarbonyl and $C_1$-$C_6$-alkoxycarbonyl can be substituted with one to two identical or different radicals selected from the group consisting of hydroxy, methoxy, hydroxycarbonyl, methoxycarbonyl, amino, mono- and di-$C_1$-$C_4$-alkylamino, $R^5$ represents methyl, $R^6$ represents a group of the formula

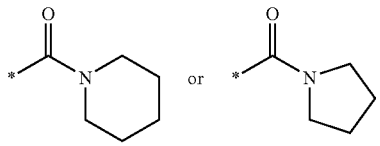

which are substituted by one or two radicals independently selected from the group consisting of $C_1$-$C_4$-alkyl, hydroxy, $C_1$-$C_4$-alkoxy, hydroxycarbonyl, $C_1$-$C_4$-alkoxycarbonyl, $C_1$-$C_4$-alkoxycarbonylamino, oxo, pyrrolidino, piperidino and morpholino, a group of the formula

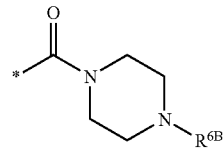

wherein $R^{6B}$ is selected from the group consisting of phenyl or pyridyl each of which can be further substituted by up to three radicals independently selected from the group consisting of fluoro, chloro, trifluoromethyl, nitro, cyano, $C_1$-$C_4$-alkyl, hydroxycarbonyl, $C_1$-$C_4$-alkoxycarbonyl and $C_1$-$C_4$-alkylcarbonyl, $C_1$-$C_4$-alkyl which is substituted by hydroxy, $C_1$-$C_4$-alkoxy, di-$C_1$-$C_4$-alkylamino, hydroxycarbonyl, $C_1$-$C_4$-alkoxycarbonyl, tetrahydrofuryl, morpholinyl, thienyl or by phenyl which for its part can be further substituted by up to three radicals independently selected from the group consisting of $C_1$-$C_4$-alkyl, fluoro, chloro and hydroxycarbonyl, and $C_1$-$C_4$-alkoxycarbonyl, mono- or di-$C_1$-$C_4$-alkylaminocarbonyl wherein the alkyl moiety or at least one alkyl moiety, respectively, is substituted by phenyl, pyridyl or pyrimidinyl each of which are further substituted by one, two or three radicals independently selected from the group consisting of fluoro, chloro, nitro, cyano, trifluoromethyl, $C_1$-$C_4$-alkyl, hydroxy, $C_1$-$C_4$-alkoxy, trifluoromethoxy, di-$C_1$-$C_4$-alkylamino, hydroxycarbonyl and $C_1$-$C_4$-alkoxycarbonyl, $C_1$-$C_4$-alkoxy which is further substituted by hydroxy, $C_1$-$C_4$-alkoxy, di-$C_1$-$C_4$-alkylamino, $C_1$-$C_4$-alkoxycarbonyl or hydroxycarbonyl, or by a group of the formula

wherein $R^{6E}$ represents $C_1$-$C_4$-alkyl, $C_1$-$C_4$-alkylcarbonyl, $C_1$-$C_4$-alkoxycarbonyl or phenyl which for its part can be further substituted by fluoro, chloro, $C_1$-$C_4$-alkyl or $C_1$-$C_4$-alkoxy, or N—$C_1$-$C_4$-alkyl-N—$C_3$-$C_6$-cycloalkylaminocarbonyl wherein the alkyl moiety can be further substituted by phenyl, furyl, pyridyl, hydroxycarbonyl or $C_1$-$C_4$-alkoxycarbonyl, $R^7$ represents hydrogen, halogen, nitro, cyano, trifluoromethyl, trifluoromethoxy, methyl or ethyl, and $Y^1, Y^2, Y^3, Y^4$ and $Y^5$ each represent CH.

In another very particular preferred embodiment, the present invention relates to compounds of general formula (I), wherein A represents a phenyl ring, $R^1$ represents hydrogen, $R^2$ represents cyano, bromo or nitro, $R^3$ represents hydrogen, R⁴ represents $C_1$-$C_4$-alkylcarbonyl, $C_1$-$C_4$-alkoxycarbonyl or cyano, wherein $C_1$-$C_4$-alkylcarbonyl and $C_1$-$C_4$-alkoxycarbonyl can be substituted with hydroxycarbonyl or $C_1$-$C_4$-alkoxycarbonyl, R⁵ represents methyl, R⁶ represents a group of the formula

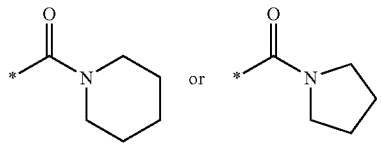

which are substituted by one or two radicals independently selected from the group consisting of $C_1$-$C_4$-alkyl, hydroxy, $C_1$-$C_4$-alkoxy, hydroxycarbonyl, $C_1$-$C_4$-alkoxycarbonyl, $C_1$-$C_4$-alkoxycarbonylamino, oxo, pyrrolidino, piperidino and morpholino, a group of the formula

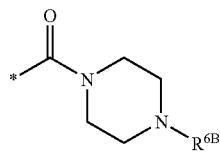

wherein $R^{6B}$ is selected from the group consisting of phenyl or pyridyl each of which can be further substituted by up to three radicals independently selected from the group consisting of fluoro, chloro, trifluoromethyl, nitro, cyano, $C_1$-$C_4$-alkyl, hydroxycarbonyl, $C_1$-$C_4$-alkoxycarbonyl and $C_1$-$C_4$-alkylcarbonyl, $C_1$-$C_4$-alkyl which is substituted by hydroxy, $C_1$-$C_4$-alkoxy, di-$C_1$-$C_4$-alkylamino, hydroxycarbonyl, $C_1$-$C_4$-alkoxycarbonyl, tetrahydrofuryl, morpholinyl, thienyl or by phenyl which for its part can be further substituted by up to three radicals independently selected from the group consisting of $C_1$-$C_4$-alkyl, fluoro, chloro and hydroxycarbonyl, and $C_1$-$C_4$-alkoxycarbonyl, mono- or di-$C_1$-$C_4$-alkylaminocarbonyl wherein the alkyl moiety or at least one alkyl moiety, respectively, is substituted by phenyl, pyridyl or pyrimidinyl each of which are further substituted by one, two or three radicals independently selected from the group consisting of fluoro, chloro, nitro, cyano, trifluoromethyl, $C_1$-$C_4$-alkyl, hydroxy, $C_1$-$C_4$-alkoxy, trifluoromethoxy, di-$C_1$-$C_4$-alkylamino, hydroxycarbonyl and $C_1$-$C_4$-alkoxycarbonyl, $C_1$-$C_4$-alkoxy which is further substituted by hydroxy, $C_1$-$C_4$-alkoxy, di-$C_1$-$C_4$-alkylamino, $C_1$-$C_4$-alkoxycarbonyl or hydroxycarbonyl, or by a group of the formula

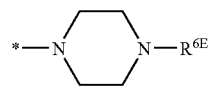

wherein $R^{6E}$ represents $C_1$-$C_4$-alkyl, $C_1$-$C_4$-alkylcarbonyl, $C_1$-$C_4$-alkoxycarbonyl or phenyl which for its part can be further substituted by fluoro, chloro, $C_1$-$C_4$-alkyl or $C_1$-$C_4$-alkoxy, or N—$C_1$-$C_4$-alkyl-N—$C_3$-$C_6$-cycloalkylaminocarbonyl wherein the alkyl moiety can be further substituted by phenyl, furyl, pyridyl, hydroxycarbonyl or $C_1$-$C_4$-alkoxycarbonyl, R⁷ represents trifluoromethyl or nitro, and $Y^1, Y^2, Y^3, Y^4$ and $Y^5$ each represent CH.

In another likewise preferred embodiment, the present invention relates to compounds according to general formula (I), wherein A is phenyl.

In another likewise preferred embodiment, the present invention relates to compounds according to general formula (I), wherein $R^1$ is hydrogen.

In another likewise preferred embodiment, the present invention relates to compounds according to general formula (I), wherein $R^2$ is cyano, especially wherein A is phenyl and $R^2$ is cyano located in para-position relative to the dihydropyridinone ring.

In another likewise preferred embodiment, the present invention relates to compounds according to general formula (I), wherein $R^3$ is hydrogen.

In another likewise preferred embodiment, the present invention relates to compounds according to general formula (I), wherein $R^4$ is acetyl, methoxycarbonyl, ethoxycarbonyl or cyano.

In another likewise preferred embodiment, the present invention relates to compounds according to general formula (I), wherein $R^5$ is methyl.

In another likewise preferred embodiment, the present invention relates to compounds according to general formula (I), wherein $R^7$ is trifluoromethyl or nitro.

In another likewise particular preferred embodiment, the present invention relates to compounds of general formula (IA)

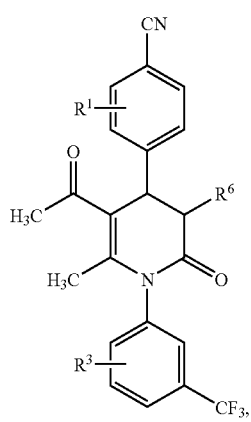

wherein $R^1$, $R^3$ and $R^6$ have the meaning indicated above.

The compounds of the present invention can enolize into the corresponding enoles:

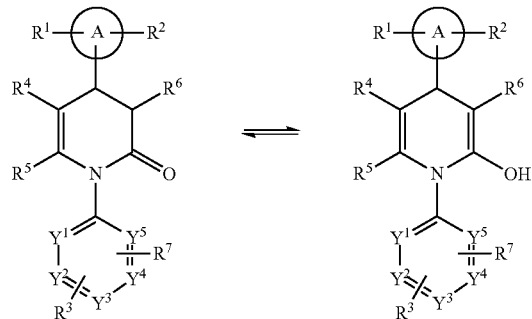

In another embodiment, the present invention relates to processes for synthesizing the compounds of general formula (I), characterized in that

[A] compounds of general formula (II)

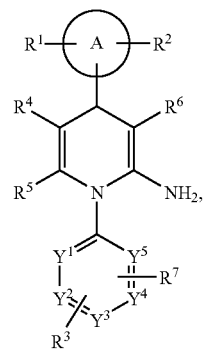

(II)

wherein $R^1$ to $R^7$, A and $Y^1$ to $Y^5$ have the meaning described above, are hydrolyzed with water,
or
[B] compounds of general formula (III)

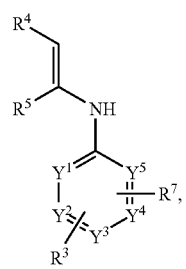

(III)

wherein $R^3$, $R^4$, $R^5$, $R^7$, and $Y^1$ to $Y^5$ have the meaning described above,
are reacted with compounds of general formula (IV)

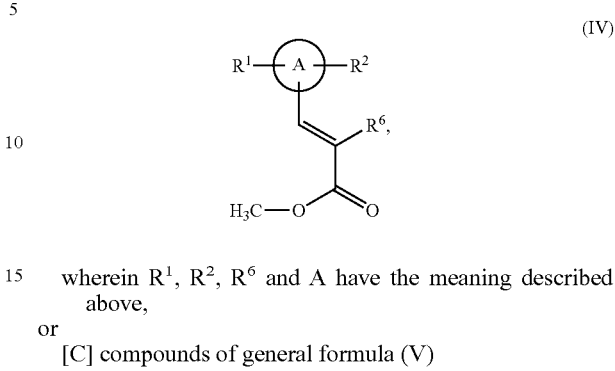

(IV)

wherein $R^1$, $R^2$, $R^6$ and A have the meaning described above,
or
[C] compounds of general formula (V)

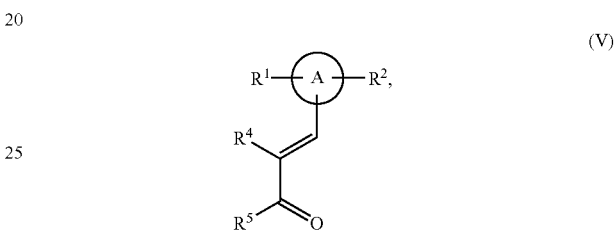

(V)

wherein $R^1$, $R^2$, $R^4$, $R^5$ and A have the meaning described above,
are reacted with compounds of general formula (VI)

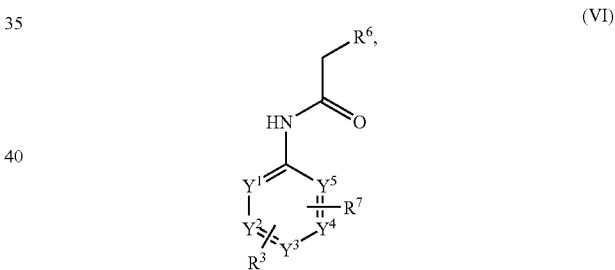

(VI)

wherein $R^3$, $R^6$, $R^7$, and $Y^1$ to $Y^5$ have the meaning described above,
in the presence of a base, such as N-tetrabutylammoniumfluoride or lithium diisopropylamide, to give compounds of general formula (VII)

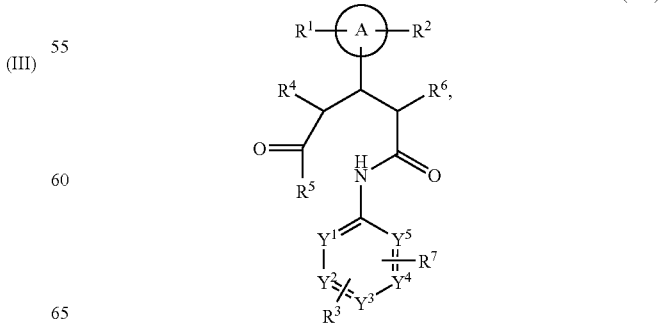

(VII)

wherein $R^1$ to $R^5$, $R^6$, $R^7$, A, and $Y^1$ to $Y^5$ have the meaning described above, which are then cyclized to compounds of general formula (I) in the presence of an acidic ion exchange resin, such as Amberlyst®-15, and a dehydrating agent, such as magnesium sulfate.

Process [A]

Suitable solvents for the process are generally customary organic solvents which do not change under the reaction conditions. These include ethers such as diethyl ether, diisopropyl ether, 1,2-dimethoxyethane, dioxan or tetrahydrofuran, ethylacetate, acetone, acetonitrile, dimethylsulfoxide, dimethylformamide, or alcohols such as methanol, ethanol, n-propanol, isopropanol, n-butanol or t-butanol, or hydrocarbons such as pentane, hexane, cyclohexane, benzene, toluene or xylene, or halogeno-hydrocarbons such as dichloromethane, dichloroethane, trichloromethane or chlorobenzene. It is also possible to use mixtures of the above-mentioned solvents. Preferred for the process is water and acetic acid.

The process can take place in the presence of an acid. Suitable acids for the process are generally inorganic or organic acids. These preferably include carboxylic acids, such as, for example acetic acid or trifluoroacetic acid, or sulfonic acids, such as, for example, methanesulfonic acid or p-toluenesulfonic acid. Preference is given to acetic acid or trifluoroacetic acid. The acid is employed in an amount from 0.25 mol to 100 mol, relative to 1 mol of the compound of the general formula (II).

The process is in general carried out in a temperature range from +20° C. to +150° C., preferably from +60° C. to +130° C.

The process is generally carried out at normal pressure. However, it is also possible to carry it out at elevated pressure or at reduced pressure (for example in a range from 0.5 to 5 bar).

The compounds of general formula (II) can be synthesized by condensing compounds of general formula (III)

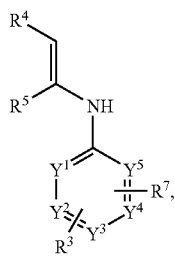

wherein $R^3$, $R^4$, $R^5$, $R^7$, and $Y^1$ to $Y^5$ have the meaning described above, in the presence of a base, in a three-component-reaction, with compounds of the general formulas (VIII) and (IX)

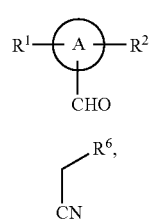

wherein $R^1$, $R^2$, $R^6$ and A have the meaning described above.

Alternatively, compounds of the general formulas (VIII) and (IX) can be reacted first, and the resulting product is then reacted with or without isolation with compounds of the general formula (III) in a second step.

Suitable solvents for the process are generally customary organic solvents which do not change under the reaction conditions. These include ethers such as diethyl ether, diisopropyl ether, 1,2-dimethoxyethane, dioxan or tetrahydrofuran, ethylacetate, acetone, acetonitrile, dimethylsulfoxide, dimethylformamide, or alcohols such as methanol, ethanol, n-propanol, isopropanol, n-butanol or t-butanol, or hydrocarbons such as pentane, hexane, cyclohexane, benzene, toluene or xylene, or halogeno-hydrocarbons such as dichloromethane, dichloroethane, trichloromethane or chlorobenzene. It is also possible to use mixtures of the above-mentioned solvents. Preferred for the process is ethanol.

Suitable bases for the process are generally inorganic or organic bases. These preferably include cyclic amines, such as, for example, piperidine, morpholine, N-methylmorpholine, pyridine or 4-N,N-dimethylaminopyridine, or $(C_1-C_4)$-trialkyl-amines, such as, for example, triethylamine or diisopropylethylamine. Preference is given to piperidine. The base is employed in an amount from 0.1 mol to 10 mol, preferably from 0.1 mol to 1 mol, relative to 1 mol of the compound of the general formula (III).

The process is in general carried out in a temperature range from +20° C. to +150° C., preferably from +60° C. to +130° C.

The process is generally carried out at normal pressure. However, it is also possible to carry it out at elevated pressure or at reduced pressure (for example in a range from 0.5 to 5 bar).

The compounds of general formula (III) can be synthesized by reacting compounds of general formula (X)

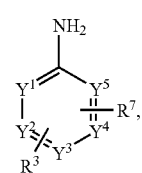

wherein $R^3$, $R^7$, and $Y^1$ to $Y^5$ have the meaning described above, with compounds of the general formula (XI)

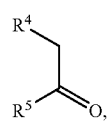

wherein $R^4$ and $R^5$ have the meaning described above.

Suitable solvents for the process are generally customary organic solvents which do not change under the reaction conditions. These include ethers such as diethyl ether, diisopropyl ether, 1,2-dimethoxyethane, dioxan or tetrahydrofuran, ethylacetate, acetone, acetonitrile, dimethylsulfoxide, dimethylformamide, or alcohols such as methanol, ethanol, n-propanol, isopropanol, n-butanol or t-butanol, or hydrocarbons such as pentane, hexane, cyclohexane, benzene, toluene or xylene, or halogeno-hydrocarbons such as dichloromethane, dichloroethane, trichloromethane or chlorobenzene. For the process also acetic acid can be employed as solvent. It is also possible to use mixtures of the above-mentioned solvents. Preferred for the process is ethanol, toluene or benzene.

Suitable acids for the process are generally inorganic or organic acids. These preferably include carboxylic acids, such as, for example acetic acid or trifluoroacetic acid, or sulfonic acids, such as, for example, methanesulfonic acid or p-toluenesulfonic acid. Preference is given to acetic acid or trifluoroacetic acid. The acid is employed in an amount from 0.25 mol to 100 mol, relative to 1 mol of the compounds of the general formulas (X) and (XI), respectively.

The process is in general carried out in a temperature range from +20° C. to +150° C., preferably from +60° C. to +130° C.

The process is generally carried out at normal pressure. However, it is also possible to carry it out at elevated pressure or at reduced pressure (for example in a range from 0.5 to 5 bar).

The compounds of the general formulas (VIII), (IX), (X) and (XI) are known per se, or they can be prepared by customary methods.

Process [B]

For process [B], compounds of the general formula (IV) can be prepared in situ, or in a first step compounds of the general formulas (VIII) and (XII) can be reacted, and the resulting product is reacted with compounds of the general formulas (III) in a second step.

Suitable solvents for the process are generally customary organic solvents which do not change under the reaction conditions. These include ethers such as diethyl ether, diisopropyl ether, 1,2-dimethoxyethane, dioxan or tetrahydrofuran, ethylacetate, acetone, acetonitrile, dimethylsulfoxide, dimethylformamide, or alcohols such as methanol, ethanol, n-propanol, isopropanol, n-butanol or t-butanol, or hydrocarbons such as pentane, hexane, cyclohexane, benzene, toluene or xylene, or halogeno-hydrocarbons such as dichloromethane, dichloroethane, trichloromethane or chlorobenzene. It is also possible to use mixtures of the above-mentioned solvents. Preferred for the process is ethanol.

Suitable bases for the process are generally inorganic or organic bases. These preferably include cyclic amines, such as, for example, piperidine, morpholine, N-methylmorpholine, pyridine or 4-N,N-dimethylaminopyridine, or $(C_1-C_4)$-trialkyl-amines, such as, for example, triethylamine or diisopropylethylamine. Preference is given to piperidine. The base is employed in an amount from 0.1 mol to 10 mol, preferably from 0.1 mol to 1 mol, relative to 1 mol of the compound of the general formula (III).

The process is in general carried out in a temperature range from +20° C. to +150° C., preferably from +60° C. to +130° C.

The process is generally carried out at normal pressure. However, it is also possible to carry it out at elevated pressure or at reduced pressure (for example in a range from 0.5 to 5 bar).

The compounds of the general formula (IV) are known per se, or they can be prepared by reacting compounds of general formula (VIII), wherein $R^1$, $R^2$ and A have the meaning described above, with compounds of general formula (XII)

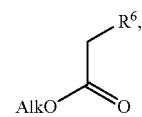

(XII)

wherein $R^6$ has the meaning described above and Alk stands for alkyl, in the presence of a base.

Suitable solvents for the process are generally customary organic solvents which do not change under the reaction conditions. These include ethers such as diethyl ether, diisopropyl ether, 1,2-dimethoxyethane, dioxan or tetrahydrofuran, ethylacetate, acetone, acetonitrile, dimethylsulfoxide, dimethylformamide, or alcohols such as methanol, ethanol, n-propanol, isopropanol, n-butanol or t-butanol, or hydrocarbons such as pentane, hexane, cyclohexane, benzene, toluene or xylene, or halogeno-hydrocarbons such as dichloromethane, dichloroethane, trichloromethane or chlorobenzene. It is also possible to use mixtures of the above-mentioned solvents. Preferred for the process is methanol, ethanol or toluene.

Suitable bases for the process are generally inorganic or organic bases. These preferably include cyclic amines, such as, for example, piperidine, morpholine, N-methylmorpholine, pyridine or 4-N,N-dimethylaminopyridine, or $(C_1-C_4)$-trialkyl-amines, such as, for example, triethylamine or diisopropylethylamine. Preference is given to piperidine. The base is employed in an amount from 0.1 mol to 10 mol, preferably from 1 mol to 3 mol, relative to 1 mol of the compound of the general formula (XII).

The process is in general carried out in a temperature range from +20° C. to +150° C., preferably from +60° C. to +130° C.

The process is generally carried out at normal pressure. However, it is also possible to carry it out at elevated pressure or at reduced pressure (for example in a range from 0.5 to 5 bar).

The compounds of the general formula (XII) are known per se, or they can be prepared by customary methods.

Process [C]

The reaction (V)+(VI)→(VII) is preferably carried out at room temperature in tetrahydrofuran as solvent. The reaction (VII)→(I) is preferably carried out in alcoholic solvents, such as methanol or ethanol, at a temperature range from +20° C. to +80° C.

The process is generally carried out at normal pressure. However, it is also possible to carry it out at elevated pressure or at reduced pressure (for example in a range from 0.5 to 5 bar). The compounds of the general formula (V) are available by Knoevenagel condensation between the compounds of general formula (VIII) and (XI).

The compounds of the general formula (VI) can be synthesized following the reaction sequence illustrated in Scheme 1:

Scheme 1

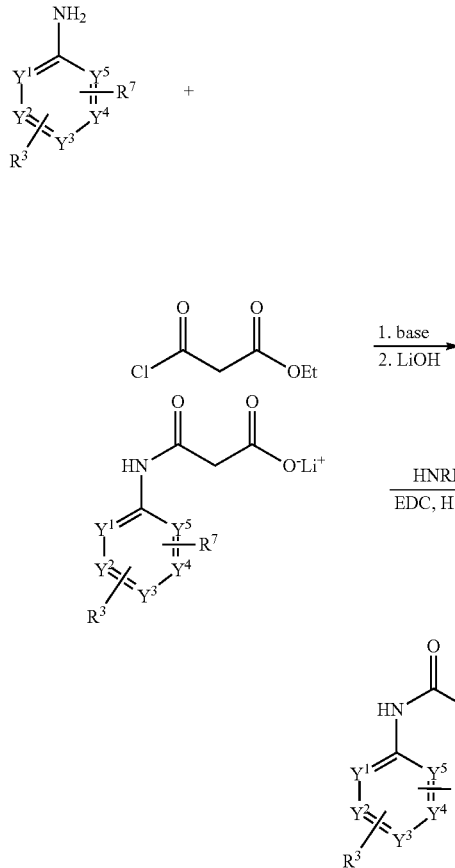

[EDC=N'-(3-dimethylaminopropyl)-N-ethylcarbodiimide x HCl; HOBt=1-hydroxy-1H-benzotriazole x $H_2O$].

In a variation of process [C], the compounds of general formula (I) can also be synthesized by reacting compounds of general formula (V) with compounds of general formula (XIII)

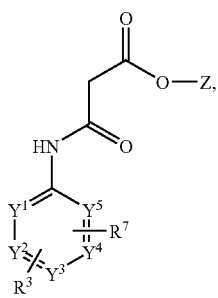

(XIII)

wherein $R^3$, $R^7$, and $Y^1$ to $Y^5$ have the meaning described above, and Z represents benzyl or allyl, in the two-step sequence described above to give compounds of general formula (XIV)

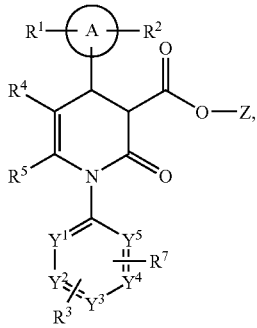

(XIV)

wherein $R^1$ to $R^5$, $R^7$, A, $Y^1$ to $Y^5$, and Z have the meaning described above,
which are then converted by hydrogenolysis (for Z=benzyl) or palladium-catalyzed allyl ester cleavage (for Z=allyl) into carboxylic acids of general formula (XV)

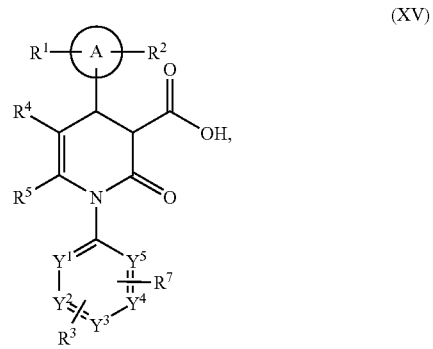

(XV)

wherein $R^1$ to $R^5$, $R^7$, A, and $Y^1$ to $Y^5$ have the meaning described above,
and subsequently coupled with primary or secondary amines (as comprised in the definition of $R^6$ as described above) in the presence of a condensing agent and a base to give the amide derivatives of general formula (I).

The hydrogenolysis reaction in step (XIV)→(XV) (for Z=benzyl) is preferably carried out at room temperature in tetrahydrofuran as solvent using palladium as hydrogenation catalyst. The reaction is generally carried out at normal pressure. However, it is also possible to carry it out at elevated pressure (for example in a range from 1 to 10 bar).

The allyl ester cleavage in step (XIV)→(XV) (for Z=allyl) is preferably carried out at room temperature in tetrahydrofuran as solvent using tetrakis(triphenylphosphine)palladium (0) as catalyst in combination with morpholine.

Suitable solvents for the amide forming reaction in step (XV)→(I) are generally customary organic solvents which do not change under the reaction conditions. These include ethers such as diethyl ether, diisopropyl ether, 1,2-dimethoxyethane, dioxan or tetrahydrofuran, or hydrocarbons such as pentane, hexane, cyclohexane, benzene, toluene or xylene, or halogeno-hydrocarbons such as dichloromethane, 1,2-dichloroethane, trichloromethane, tetrachloromethane or chlorobenzene, or other solvents such as ethyl acetate, acetonitrile, pyridine, dimethylsulfoxide, N,N-dimethylformamide, N,N'-dimethylpropylene urea (DMPU) or N-methylpyrrolidone (NMP). It is also possible to use mixtures of the above-mentioned solvents. Preferred for the process is dimethylsulfoxide.

Suitable coupling agents for the amide forming reaction in step (XV)→(I) include, for instance, carbodiimides such as N,N'-diethyl-, N,N'-dipropyl-, N,N'-diisopropyl-, N,N'-dicyclohexylcarbodiimide (DCC), N-(3-dimethylaminoisopropyl)-N'-ethylcarbodiimide hydrochloride (EDC), or phosgene derivatives such as N,N'-carbonyldiimidazole, or 1,2-oxazolium compounds such as 2-ethyl-5-phenyl-1,2-oxazolium-3-sulfate or 2-tert.-butyl-5-methyl-isoxazolium-perchlorate, or acylamino derivatives such as 2-ethoxy-1-ethoxycarbonyl-1,2-dihydroquinoline, or agents such as isobutylchloroformate, propanephosphonic acid anhydride, cyanophosphonic acid diethyl ester, bis-(2-oxo-3-oxazolidinyl)-phosphorylchloride, benzotriazol-1-yloxy-tris(dimethylamino)phosphonium-hexafluorophosphate, benzotriazol-1-yloxy-tris(pyrrolidino)phosphonium-hexafluorophosphate (PyBOP), O-(benzotriazol-1-yl)-N,N,N',N'-tetramethyluronium-hexafluorophosphate (HBTU), O-(benzotriazol-1-yl)-N,N,N',N'-tetramethyluronium-tetrafluoroborate (TBTU), 2-(2-oxo-1-(2H)-pyridyl)-1,1,3,3-tetramethyluronium-tetrafluoroborate (TPTU) or O-(7-azabenzotriazol-1-yl)-N,N,N',N'-tetramethyluronium-hexafluorophosphate (HATU), optionally in combination with auxiliary agents such as 1-hydroxybenzotriazole (HOBt) or N-hydroxysuccinimide (HOSu), and with bases such as alkali carbonates, e.g. sodium or potassium carbonate or hydrogencarbonate, or organic bases such as trialkyl amines or cyclic amines, e.g. triethylamine, N-methylmorpholine, N-methylpiperidine, N,N-diisopropylethylamine or pyridine. Preferred for the process is TBTU in combination with N,N-diisopropylethylamine.

The amide forming reaction in step (XV)→(I) is generally carried out in a temperature range from 0° C. to +100° C., preferably from 0° C. to +40° C. The process is generally carried out at normal pressure. However, it is also possible to carry it out at elevated pressure or at reduced pressure (for example in a range from 0.5 to 5 bar).

The above-mentioned methods can be illustrated by the following Scheme 2:

Scheme 2

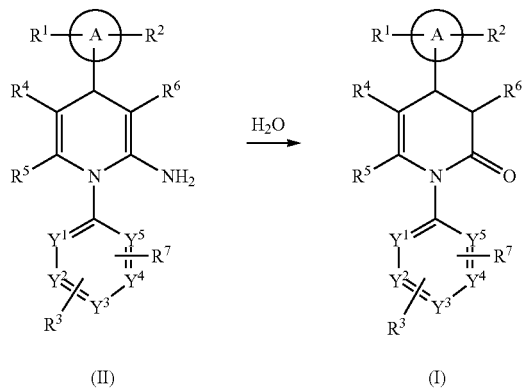

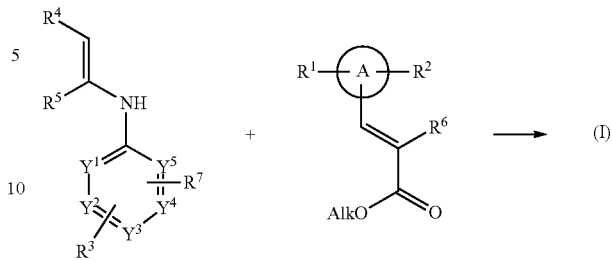

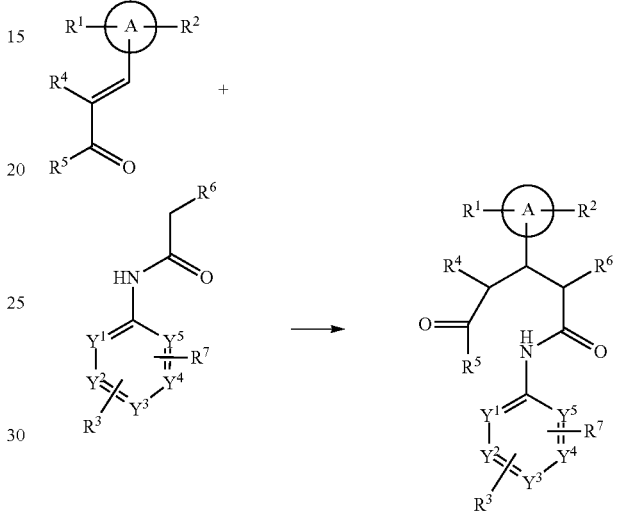

The compounds according to the invention exhibit an unforeseeable, useful pharmacological and pharmacokinetic activity spectrum.

They are therefore suitable for use as medicaments for the treatment and/or prophylaxis of disorders in humans and animals.

Surprisingly, the compounds of the present invention show human neutrophil elastase (HNE) inhibitory activity and are therefore suitable for the preparation of medicaments for the treatment of diseases associated with HNE activity. They may thus provide an effective treatment of acute and chronic inflammatory processes, such as rheumatoid arthritis, atherosclerosis, and especially of acute and chronic pulmonary diseases, such as lung fibrosis, cystic fibrosis, pneumonia, acute respiratory distress syndrome (ARDS), in particular pulmonary emphysema, including smoking-induced emphysema, and chronic obstructive pulmonary diseases (COPD), chronic bronchitis and bronchiectasis. The compounds of the present invention may further provide an effective treatment for cardiovascular ischaemic diseases such as acute coronary syndrome, acute myocardial infarction, unstable and stable angina pectoris, coronary artery bypass grafts (CABG) and heart failure development, for atherosclerosis, mitral valvular disease, atrial septal defects, percutaneous transluminal coronary angioplasty (PTCA), inflammation after open heart surgery and for, pulmonary hypertension. They may also prove useful for an effective treatment of rheumatoid arthritis, acute inflammatory arthritis, cancer, acute pancreatitis, ulcerative colitis, periodontal disease, Chury-Strauss syndrome, acute and chronic atopic dermatitis, psoriasis, systemic lupus erythematosus, bullous pemphigus, sepsis, alcoholic hepatitis, liver fibrosis, Behcet's disease, allergic fungal sinusitis, allergic sinusitis, Crohn's disease, Kawasaki disease, glomerulonephritis, acute pyelonephritis, colorectal diseases, chronic suppurative otitis media, chronic venous leg ulcers, inflammatory bowel disease, bacterial and viral infections, brain trauma, stroke and other conditions in which neutrophil participation is involved.

The present invention further provides medicaments containing at least one compound according to the invention, preferably together with one or more pharmacologically safe excipient or carrier substances, and also their use for the abovementioned purposes.

The active component can act systemically and/or locally. For this purpose, it can be applied in a suitable manner, for example orally, parenterally, pulmonally, nasally, sublingually, lingually, buccally, rectally, transdermally, conjunctivally, otically or as an implant.

For these application routes, the active component can be administered in suitable application forms.

Useful oral application forms include application forms which release the active component rapidly and/or in modified form, such as for example tablets (non-coated and coated tablets, for example with an enteric coating), capsules, sugar-coated tablets, granules, pellets, powders, emulsions, suspensions, solutions and aerosols.

Parenteral application can be carried out with avoidance of an absorption step (intravenously, intraarterially, intracardially, intraspinally or intralumbarly) or with inclusion of an absorption (intramuscularly, subcutaneously, intracutaneously, percutaneously or intraperitoneally). Useful parenteral application forms include injection and infusion preparations in the form of solutions, suspensions, emulsions, lyophilisates and sterile powders.

Forms suitable for other application routes include for example inhalatory pharmaceutical forms (including powder inhalers, nebulizers), nasal drops/solutions, sprays; tablets or capsules to be administered lingually, sublingually or buccally, suppositories, ear and eye preparations, vaginal capsules, aqueous suspensions (lotions, shake mixtures), lipophilic suspensions, ointments, creams, milk, pastes, dusting powders or implants.

The active components can be converted into the recited application forms in a manner known per se. This is carried out using inert non-toxic, pharmaceutically suitable excipients. These include inter alia carriers (for example microcrystalline cellulose), solvents (for example liquid polyethylene glycols), emulsifiers (for example sodium dodecyl sulphate), dispersing agents (for example polyvinylpyrrolidone), synthetic and natural biopolymers (for example albumin), stabilizers (for example antioxidants such as ascorbic acid), colorants (for example inorganic pigments such as iron oxides) or taste and/or odor corrigents.

For human use, in the case of oral administration, it is recommendable to administer doses of from 0.001 to 50 mg/kg, preferably of 0.01 mg/kg to 20 mg/kg. In the case of parenteral administration, such as, for example, intravenously or via mucous membranes nasally, buccally or inhalationally, it is recommendable to use doses of 0.001 mg/kg to 0.5 mg/kg.

In spite of this, it can be necessary in certain circumstances to depart from the amounts mentioned, namely as a function of body weight, application route, individual behaviour towards the active component, manner of preparation and time or interval at which application takes place. It can for instance be sufficient in some cases to use less than the aforementioned minimum amount, while in other cases the upper limit mentioned will have to be exceeded. In the case of the application of larger amounts, it can be advisable to divide them into a plurality of individual doses spread through the day.

The percentages in the tests and examples which follows are, unless otherwise stated, by weight; parts are by weight. Solvent ratios, dilution ratios and concentrations reported for liquid/liquid solutions are each based on the volume.

A. Evaluation of Physiological Activity

The potential of the compounds of the invention to inhibit neutrophil elastase activity may be demonstrated, for example, using the following assays:

I. In vitro Enzyme Assays of Human Neutrophil Elastase (HNE)

Assay Contents assay buffer: 0.1 M HEPES-NaOH buffer pH 7.4, 0.5 M NaCl, 0.1% (w/v) bovine serum albumin;

suitable concentration (see below) of HNE (18 U/mg lyophil., #20927.01, SERVA Electrophoresis GmbH, Heidelberg, Germany) in assay buffer;

suitable concentration (see below) of substrate in assay buffer;

suitable concentration of test compounds diluted with assay buffer from a 10 mM stock solution in DMSO.

Example I-A

In vitro Inhibition of HNE Using a Fluorogenic Peptide Substrate (Continuous Read-out Signal, 384 MTP Assay Format):

In this protocol, the elastase substrate MeOSuc-Ala-Ala-Pro-Val-AMC (#324740, Calbiochem-Novabiochem Corporation, Merck KGaA, Darmstadt, Germany) is used. The test solution is prepared by mixing 10 µl of test compound dilution, 20 µl of HNE enzyme dilution (final concentration 8-0.4 µU/ml, routinely 2.1 µU/ml) and 20 µl of substrate dilution (final concentration 1 mM-1 µM, routinely 20 µM), respectively. The solution is incubated for 0-2 hrs at 37° C. (routinely one hour). The fluorescence of the liberated AMC due to the enzymatic reaction is measured at 37° C. (TECAN spectra fluor plus plate reader). The rate of increase of the fluorescence (ex. 395 nm, em. 460 nm) is proportional to elastase activity. $IC_{50}$ values are determined by RFU-versus-[I] plots. $K_m$ and $K_{m(app.)}$ values are determined by Lineweaver-Burk plots and converted to $K_i$ values by Dixon plots.

The preparation examples have $IC_{50}$ values within the range of 10 nM-1 µM in this assay. Representative data are given in Table 1:

TABLE 1

| Example No. | $IC_{50}$ [nM] |
|---|---|
| 19 | 40 |
| 22 | 80 |
| 23 | 80 |
| 24 | 80 |
| 27 | 30 |
| 28 | 80 |
| 34 | 60 |
| 45 | 70 |

TABLE 1-continued

| Example No. | IC$_{50}$ [nM] |
|---|---|
| 54 | 60 |
| 61 | 50 |

Example I-B

In vitro Inhibition of HNE Using a Fluorogenic, Unsoluble Elastin Substrate (Discontinuous Read-out Signal, 96 MTP Assay Format):

In this protocol the elastase substrate elastin-fluorescein (#100620, ICN Biomedicals GmbH, Eschwege, Germany) is used. The test solution is prepared by mixing 3 µl of test compound dilution, 77 µl of HNE enzyme dilution (final concentration 0.22 U/ml-2.2 mU/ml, routinely 21.7 µU/ml) and 80 µl substrate suspension (final concentration 2 mg/ml). The suspension is incubated for 0-16 hrs at 37° C. (routinely four hours) under slightly shaking conditions. To stop the enzymatic reaction, 160 µl of 0.1 M acetic acid are added to the test solution (final concentration 50 mM). The polymeric elastin-fluorescein is pulled down by centrifugation (Eppendorf 5804 centrifuge, 3.000 rpm, 10 min). The supernatant is transferred into a new MTP and the fluorescence of the liberated peptide fluorescein due to the enzymatic reaction is measured (BMG Fluostar plate reader). The rate of fluorescence (ex. 490 nm, em. 520 nm) is proportional to elastase activity. IC$_{50}$ values are determined by RFU-versus-[I] plots.

II. In vitro Human Neutrophil Assays

Example II-A

In vitro PMN Elastolysis Assay:

This assay is used to determine the elastolytic potential of human polymorphonuclear cells (PMNs) and assess the proportion of degradation due to neutrophil elastase [cf. Z. W. She et al., *Am. J Respir. Cell. Mol. Biol.* 9, 386-392 (1993)]. Tritiated elastin, in suspension, is coated on to a 96 well plate at 10 µg per well. Test and reference [ZD-0892 (*J. Med. Chem.* 40, 1876-1885, 3173-3181 (1997), WO 95/21855) and α1 protease inhibitor (α1PI)] compounds are added to the wells at the appropriate concentrations. Human PMNs are separated from peripheral venous blood of healthy donors and resuspended in culture media. The neutrophils are added to the coated wells at concentrations ranging between $1\times10^6$ to $1\times10^5$ cells per well. Porcine pancreatic elastase (1.3 µM) is used as a positive control for the assay, and α1PI (1.2 µM) is used as the positive inhibitor of neutrophil elastase. The cellular, control is PMNs without compound at each appropriate cell density. The cells plus compounds are incubated in a humidified incubator at 37° C. for 4 hours. The plates are centrifuged to allow the harvest of cell supernatant only. The supernatant is transferred in 75 µl volumes to corresponding wells of a 96 well Lumaplate™ (solid scintillant containing plates). The plates are dried until no liquid is visible in the wells and read in a beta counter for 3 minutes per well.

Elastolysis of the $^3$H-elastin results in an increase in counts in the supernatant. An inhibition of this elastolysis shows a decrease, from the cellular control, of tritium in the supernatant. α1PI gave 83.46±3.97% (mean±s.e.m.) inhibition at 1.2 µM (n=3 different donors at $3.6\times10^5$ cells per well). IC$_{50}$ values were obtained for the reference compound ZD-0892 of 45.50±7.75 nM (mean±s.e.m.) (n=2 different donors at $3.6\times10^5$ cells per well).

Given that ZD-0892 is a selective inhibitor of PMN elastase along with the data from α1PI inhibition, these results indicate that the majority of elastin degradation by PMNs is due to the release of neutrophil elastase, and not to another elastolytic enzyme such as matrix metalloproteases (MMPs). The compounds of this invention are evaluated for their inhibitory activity in this HNE-dependent model of neutrophil elastolysis.

Example II-B

In vitro Inhibition of Membrane Bound Elastase:

Measurement of the inhibition of elastase bound to neutrophil membranes is performed using a human neutrophil assay. Neutrophils are stimulated with LPS at 37° C. for 35 min and then spun at 1600 rpm. Subsequently, the membrane bound elastase is fixed to the neutrophils with 3% paraformaldehyde and 0.25% glutaraldehyde for 3 min at 4° C. The neutrophils are then spun, and vehicle and the compound under evaluation are added, followed by addition of the substrate MeO-Suc-Ala-Ala-Pro-Val-AMC (#324740, Calbiochem-Novabiochem Corporation, Merck KGaA, Darmstadt, Germany) at 200 µM. Following a 25 min incubation at 37° C., the reaction is terminated with PMSF (phenylmethanesulfonyl fluoride), and the fluorescence is read at ex: 400 nm and em: 505 nm. IC$_{50}$ values are determined by interpolation from plots of relative fluorescence vs. inhibitor concentration.

III. In vivo Models

Example III-A

In vivo Model of Acute Lung Injury in the Rat:

Instillation of human neutrophil elastase (HNE) into rat lung causes acute lung damage. The extent of this injury can be assessed by measuring lung haemorrhage.

Rats are anaesthetised with Hypnorm/Hypnovel/water and instilled with HNE or saline delivered by microsprayer into the lungs. Test compounds are administered by intravenous injection, by oral gavage or by inhalation at set times prior to the administration of HNE. Sixty minutes after the administration of elastase animals are killed by an anaesthetic overdose (sodium pentobarbitone) and the lungs lavaged with 2 ml heparinised phosphate buffered saline (PBS). Bronchoalveolar lavage (BAL) volume is recorded and the samples kept on ice. Each BAL sample is centrifuged at 900 r.p.m. for 10 minutes at 4-10° C. The supernatant is discarded and the cell pellet resuspended in PBS and the sample spun down again. The supernatant is again discarded and the cell pellet resuspended in 1 ml 0.1% cetyltrimethyl-ammonium bromide (CTAB)/PBS to lyse the cells. Samples are frozen until blood content is assayed. Prior to the haemorrhage assay the samples are defrosted and mixed. 100 µl of each sample are placed into a separate well of a 96 well flat-bottomed plate. All samples are tested in duplicate. 100 µl 0.1% CTAB/PBS is included as a blank. The absorbance of the well contents is measured at 415 nm using a spectrophotometer. A standard curve is constructed by measuring the OD at 415 nm of different concentrations of blood in 0.1% CTAB/PBS. Blood content values are calculated by comparison to the standard curve (included in each plate) and normalised for the volume of BAL fluid retrieved.

The compounds of this invention are evaluated intravenously, orally or by inhalation for their inhibitory activity in this model of HNE-induced haemorrhage in the rat.

Example III-B

In vivo Model of Acute Myocardial Infarction in the Rat:

Elastase inhibitors are tested in a rat thread infarct model. Male Wistar rats (weighing >300 g) receive 10 mg/kg aspirin 30 min prior to surgery. They are anaesthetized by isofluran and ventilated (120-130 strokes/min, 200-250 µl stroke volume; MiniVent Type 845, Hugo Sachs Elektronik, Germany) during the whole surgery. Following a left thoracotomy at the fourth intercostal space, the pericardium is opened and the heart briefly exteriorized. A thread is turned around the left coronary artery (LAD) without occluding the artery. The thread is passed under the skin to the neck of the animal. The thorax is closed and the animal is allowed to recover for 4 days. At the fifth day, rats are anaesthetized with ether for 3 min, and the thread is tied and the LAD occluded under ECG control. Test compounds are administered before or after LAD occlusion per os, intraperitoneally or intravenously (bolus or permanent infusion). After 1 hr occlusion, the thread is reopened to allow reperfusion. Hearts are excised, and infarct sizes are determined 48 hours later by staining of the re-occluded hearts with Evans blue, followed by TTC (triphenyltetrazolium chloride) staining of 2 mm heart sections. Normoxic (not occluded tissue) areas stain blue, ischemic (occluded but surviving tissue) areas stain red and necrotic (occluded dead tissue) areas remain white. Each tissue section is scanned and infarct sizes are determined by computer planimetry.

B. Examples

Abbreviations:

DMSO Dimethylsulfoxide

ESI electro-spray ionisation (for MS)

HPLC high pressure liquid chromatography

LC-MS liquid chromatography coupled with mass spectroscopy

Min minute(s)

MS mass spectroscopy

NMR nuclear magnetic resonance of th. of theoretical (yield)

$R_t$ retention time (for HPLC)

LC-MS Method 1

Instrument: Micromass Quattro LCZ with HPLC Agilent Series 1100; Column: Phenomenex Synergi 2µ Hydro-RP Mercury 20 mm×4 mm; Eluent A: 1 l water+0.5 ml 50% formic acid, Eluent B: 1 l acetonitrile+0.5 ml 50% formic acid; Gradient: 0.0 min 90% A→2.5 min 30% A→3.0 min 5% A→4.5 min 5% A; Flow: 0.0 min 1 ml/min→2.5 min/3.0 min/4.5 min 2 ml/min; Oven: 50° C.; UV detection: 208-400 nm.

LC-MS Method 2

Instrument MS: Micromass TOF (LCT); Instrument HPLC: 2-column-switching, Waters 2690; Column: YMC-ODS-AQ, 50 mm×4.6 mm, 3.0 µm; Eluent A: water+0.1% formic acid, Eluent B: acetonitrile+0.1% formic acid; Gradient: 0.0 min 100% A→0.2 min 95% A→1.8 min 25% A→1.9 min 10% A→2.0 min 5% A→3.2 min 5% A; Oven: 40° C.; Flow: 3.0 ml/min; UV detection: 210 nm.

HPLC Method 3

Instrument: HP 1100 with DAD detection; Column: Kromasil RP-18, 60 mm×2 mm, 3.5 µm; Eluent A: 5 ml $HClO_4$/l water, Eluent B: acetonitrile; Gradient: 0 min 2% B→0.5 min 2% B→4.5 min 90% B→6.5 min 90% B; Flow: 0.75 ml/min; Oven: 30° C.; UV detection: 210 nm.

Starting Materials:

Example 1A

Ethyl 3-oxo-3-{[3-(trifluoromethyl)phenyl]amino}propanoate

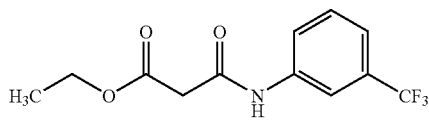

To a stirred solution of 3-trifluoromethylaniline (1.90 g, 11.8 mmol), triethylamine (1.43 g, 14.5 mmol) and 4-N,N-dimethylaminopyridine (1 mg) in dichloromethane (20 ml) is added at 0° C. ethyl malonyl chloride (1.78 g, 11.8 mmol). The reaction mixture is warmed to room temperature overnight, then allowed to stand for two days. Water (20 ml) is added and the product is extracted with dichloromethane (1 l). The organic phase is washed with saturated ammonium chloride solution (500 ml) and saturated sodium chloride solution (200 ml), dried over magnesium sulphate monohydrate, filtered and concentrated. The crude product is chromatographed over silica gel with cyclohexane/ethyl acetate mixtures as eluent.

Yield: 3 g (92% of th.)

HPLC (method 3): $R_t$=4.38 min.

MS (ESIpos): m/z=276 (M+H)$^+$ $^1$H-NMR (200 MHz, $CDCl_3$): δ=9.55 (s, 1H), 7.86 (s, 1H), 7.77 (d, 1H), 7.52-7.32 (m, 2H), 4.37-4.16 (m, 2H), 3.51 (s, 2H), 1.34 (m, 3H).

Example 2A

Lithium 3-oxo-3-{[3-(trifluoromethyl)phenyl]amino}propanoate

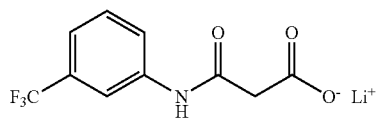

To a tetrahydrofuran (350 ml) solution of ethyl 3-oxo-3-{[3-(trifluoromethyl)phenyl]amino}propanoate (5 g, 18.17 mmol) (Example 1A) is added lithium hydroxide (435 mg, 18.17 mmol) in water (150 ml). The solution is stirred at room temperature for 4 hours, and then concentrated to afford a white solid. The crude product is used without further purification.

Yield: 4.62 g (99% of th.)

HPLC (method 3): $R_t$=3.88 min., $\lambda_{max}$ 202 nm

MS (ESIpos): m/z=254 (M+H)$^+$ $^1$H-NMR (300 MHz, DMSO-d$_6$): δ=12.84 (s, 1H), 8.10 (s, 1H), 7.66 (d, 1H), 7.51 (t, 1H), 7.33 (d, 1H), 2.90 (s, 2H).

Example 3A

Benzyl 3-oxo-3-{[3-(trifluoromethyl)phenyl]amino}propanoate

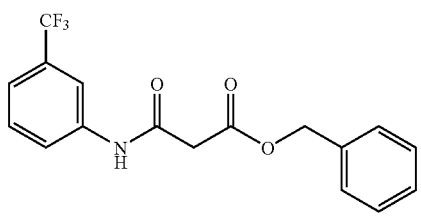

To a stirred solution of lithium 3-oxo-3-{[3-(trifluoromethyl)phenyl]amino}propanoate (2.0 g, 7.9 mmol) (Example 2A) in water (15 ml) is added a solution of Aliquat 336® (3.1 g) and benzyl bromide (1.35 g, 7.5 mmol) in dichloromethane (15 ml). The reaction mixture is stirred for two days at room temperature, then extracted with dichloromethane (500 ml). The organic phase is dried over anhydrous magnesium sulfate, filtered and concentrated in vacuo. The residue is purified by flash chromatography over silica gel 60 with cyclohexane/ethyl acetate mixtures as eluent.

Yield: 2 g (75% of th.)

MS (ESIpos): m/z=355 (M+NH$_4$)$^+$

HPLC (method 3): R$_t$=4.80 min, λ$_{max}$=204 nm $^1$H-NMR (300 MHz, CDCl$_3$): δ=9.33 (br s, 1H), 7.84-7.71 (m, 2H), 7.49-7.30 (m, 7H), 5.24 (s, 2H), 3.54 (s, 2H).

Example 4A 4-(2-Acetyl-3-oxobut-1-en-1-yl)benzonitrile

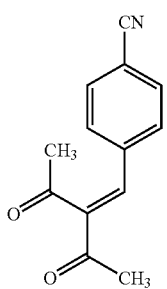

A solution of 4-cyanobenzonitrile (20 g, 0.15 mol), 2,4-pentanedione (17 g, 0.17 mol), piperidine (130 mg, 1.5 mmol) and p-toluene sulfonic acid (260 mg, 1.5 mmol) in toluene (400 ml) is refluxed overnight with a Dean-Stark trap. The solution is concentrated in vacuo and purified over silica gel with cyclohexane/ethyl acetate mixtures as eluent.

Yield: 30 g (92% of th.)

HPLC (method 3): R$_t$=3.81 min, λ$_{max}$=284 nm

MS (ESIpos): m/z=231 (M+NH$_4$)$^+$ $^1$H-NMR (300 MHz, CDCl$_3$): δ=7.68 (d, 2H), 7.49 (d, 2H), 7.44 (s, 1H), 2.44 (s, 3H), 2.28 (s, 3H).

Example 5A

Benzyl 4-acetyl-3-(4-cyanophenyl)-5-oxo-2-({[3-(trifluoromethyl)phenyl]amino}carbonyl)hexanoate

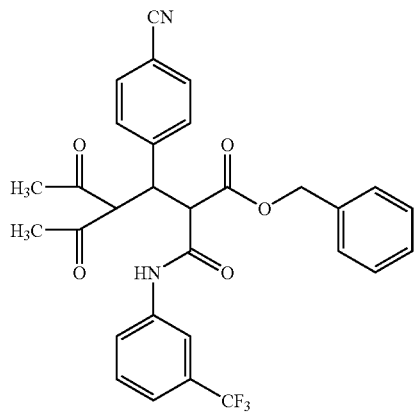

To a stirred solution of benzyl 3-oxo-3-{[3-(trifluoromethyl)phenyl]amino}propanoate (6.7 g, 19.2 mmol) (Example 3A) and 4-(2-acetyl-3-oxobut-1-en-1-yl)benzonitrile (4.2 g, 19.2 mmol) (Example 4A) in tetrahydrofuran (140 ml) is added tetrabutylammonium fluoride (9.9 ml of a 1 M solution in tetrahydrofuran). The reaction is stirred for 2 hours at room temperature, then concentrated in vacuo and chromatographed over silica gel 60 with cyclohexane/ethyl acetate mixtures as eluent. The product is isolated as a mixture of diastereomers.

Yield: 4.3 g (40% of th.)

MS (ESIpos): m/z=551 (M+H)$^+$

HPLC (method 3): R$_t$=5.07 min, λ$_{max}$=200 nm.

Example 6A

Benzyl 5-acetyl-4-(4-cyanophenyl)-6-methyl-2-oxo-1-[3-(trifluoromethyl)phenyl]-1,2,3,4-tetrahydropyridine-3-carboxylate

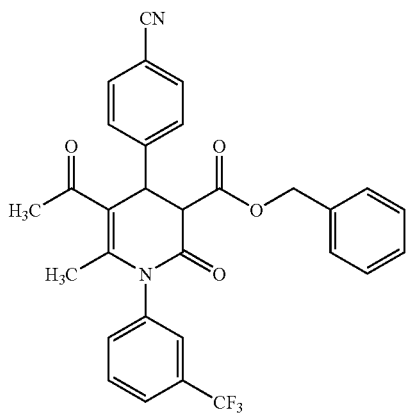

A suspension of benzyl 4-acetyl-3-(4-cyanophenyl)-5-oxo-2-({[3-(trifluoromethyl)phenyl]amino}carbonyl)hexanoate (7.5 g, 15.6 mmol) (Example 5A), anhydrous magnesium sulfate (15 g, 125 mmol) and Amberlyst 15® (7.5 g) in ethanol (300 ml) is stirred overnight at reflux. The reaction is cooled to room temperature, filtered through a pad of celite and concentrated in vacuo. The residue is purified by flash chromatography over silica gel 60 with cyclohexane/ethyl acetate mixtures as eluent.

Yield: 4.64 g (64% of th.)
HPLC (method 3): $R_t$=5.12 min, 200 nm
MS (ESIpos): m/z=533 (M+H)$^+$
$^1$H-NMR (300 MHz, CDCl$_3$): δ=7.79-6.96 (m, 13H), 5.47 (d, J=11.9 Hz, 1H), 5.12 (d, J=11.8 Hz, 1H), 4.76 (br s, 1H), 3.87 (d, J=2.3 Hz, 1H), 2.15 (s, 3H), 1.89 (s, 3H).

Example 7A

5-Acetyl4-(4-cyanophenyl)-6-methyl-2-oxo-1-[3-(trifluoromethyl)phenyl]-1,2,3,4-tetrahydropyridine-3-carboxylic acid

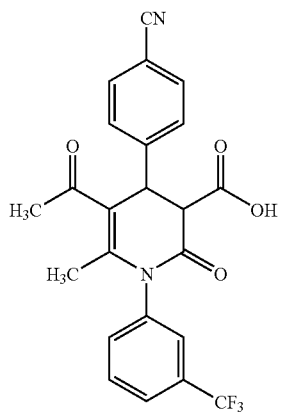

A stirred suspension of benzyl 5-acetyl-4-(4-cyanophenyl)-6-methyl-2-oxo-1-[3-(trifluoromethyl)phenyl]-1,2,3,4-tetrahydropyridine-3-carboxylate (7.5 g, 14 mmol) (Example 6A) and 10%. palladium on charcoal (255 mg) in tetrahydrofuran (975 ml) is treated with hydrogen gas at room temperature under atmospheric pressure. After 15 minutes, the reaction is stopped and the solution is filtered and concentrated. The residue is immediately used in the next step without further purification and characterisation.

Preparation Examples

General Procedure for the Preparation of Dihydropyridinone-3-carboxamide Derivatives A solution of Example 7A (0.10 mmol), N-[(1H-1,2,3-benzotriazol-1-yloxy)(dimethylamino)methylene]-N-methylmethanaminium tetrafluoroborate (0.13 mmol), diisopropylethylamine (0.20 ml) and respective amine component (0.10 mmol) in dimethylsulfoxide (0.50 ml) is stirred at room temperature overnight. The reaction mixture is filtered and the residue is purified by preparative LC-MS chromatography [sample preparation: 100 μmol in 0.8 ml DMSO; columns: Kromasil-100A C18, 50×20 mm, 5.0 μm (acidic gradients), Zorbax Extend C18, 50×20 mm, 5.0 μm (basic gradients); eluent (acidic): A=acetonitrile, B=water+0.1% formic acid; eluent (basic): A=acetonitrile, B=water+0.1% triethylamine; gradient: 0.0 min 90% B→0.75 min 90% B→5.5 min 0% B→6.5 min 0% B→7.0 min 90% B; flow rate HPLC: 40 ml/min; UV detection (2 wavelengths): 214 nm/254 nm].

Using this procedure, the following examples are obtained (the amine components employed in these reactions are commercially available, known per se or can be prepared by customary methods):

| Example No. | Structure | Yield [%] | MS (ESIpos): m/z (M + H)$^+$ | Retention time (method) |
|---|---|---|---|---|
| 1 | 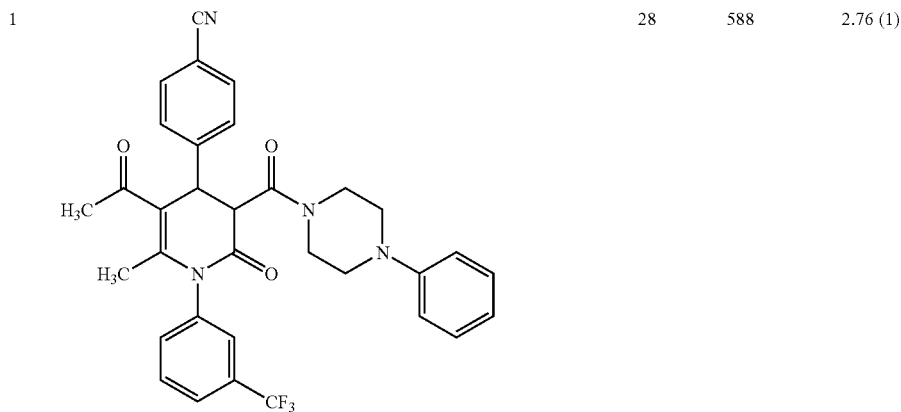 | 28 | 588 | 2.76 (1) |

-continued
| Example No. | Structure | Yield [%] | MS (ESIpos): m/z (M + H)+ | Retention time (method) |
|---|---|---|---|---|
| 2 | 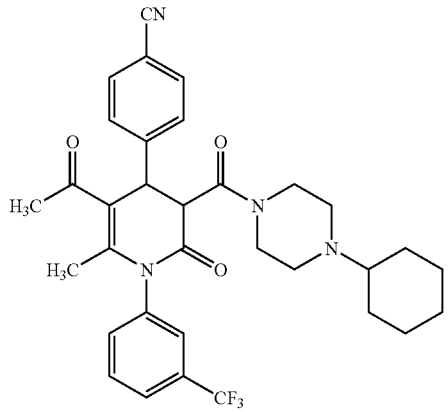 | 14 | 594 | 2.12 (1) |
| 3 | 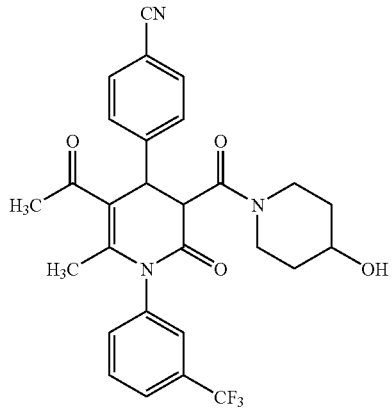 | 8 | 527 | 2.17 (1) |
| 4 | 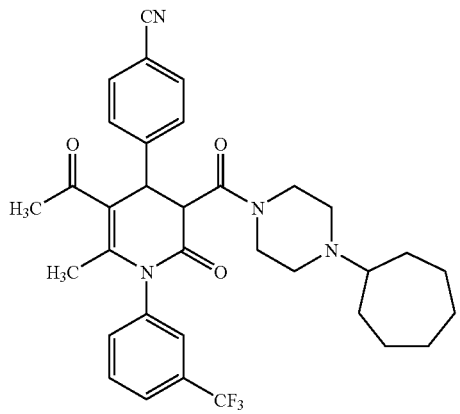 | 16 | 608 | 2.2 (1) |

-continued

| Example No. | Structure | Yield [%] | MS (ESIpos): m/z (M + H)+ | Retention time (method) |
|---|---|---|---|---|
| 5 | 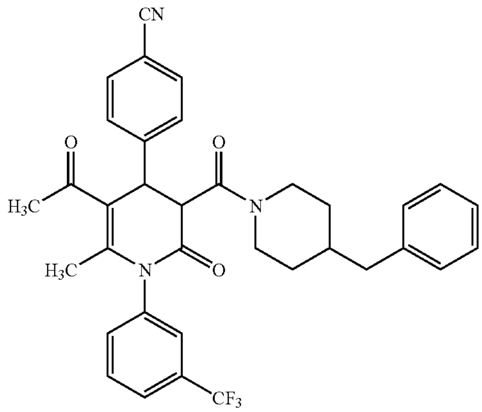 | 11 | 601 | 2.96 (1) |
| 6 | 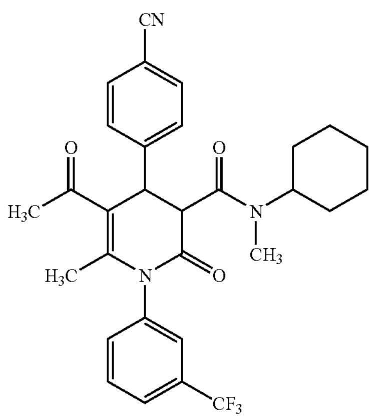 | 9 | 539 | 2.78 (1) |
| 7 | 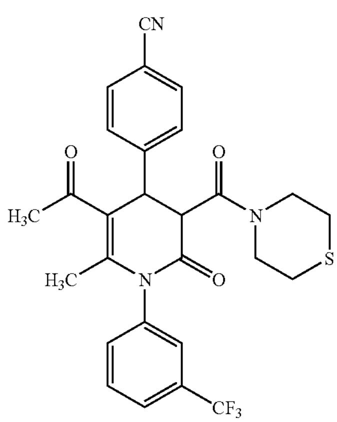 | 48 | 529 | 2.18 (2) |

-continued

| Example No. | Structure | Yield [%] | MS (ESIpos): m/z (M + H)+ | Retention time (method) |
|---|---|---|---|---|
| 8 | 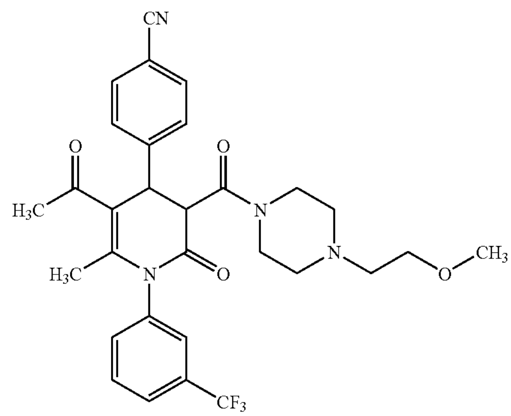 | 21 | 570 | 1.95 (1) |
| 9 | 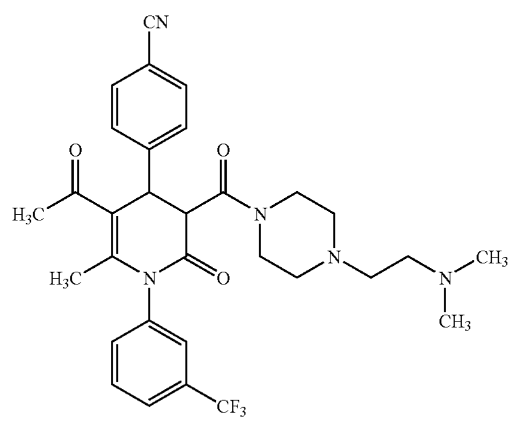 | 31 | 583 | 1.9 (1) |
| 10 | 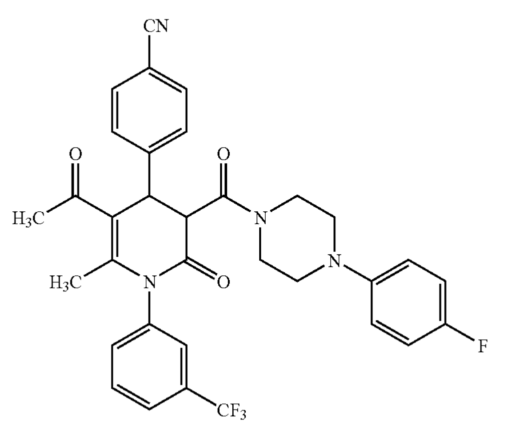 | 45 | 606 | 2.77 (1) |

-continued

| Example No. | Structure | Yield [%] | MS (ESIpos): m/z (M + H)+ | Retention time (method) |
|---|---|---|---|---|
| 11 | 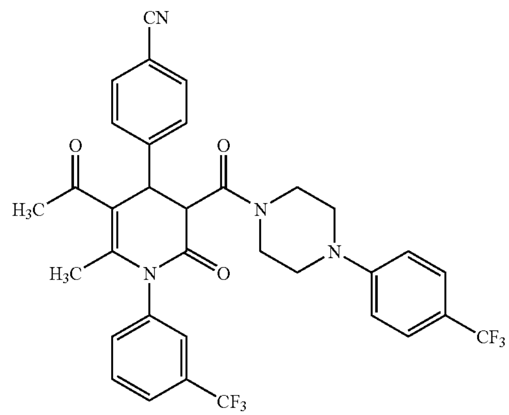 | 44 | 656 | 2.96 (1) |
| 12 | 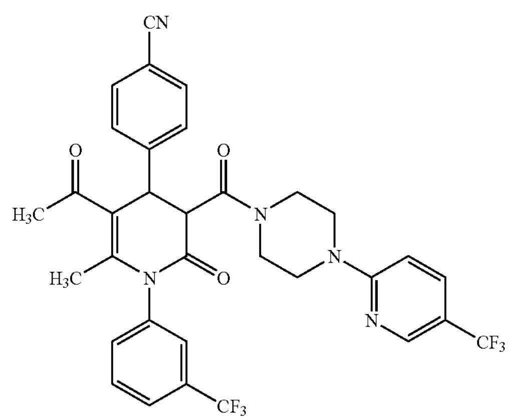 | 34 | 657 | 2.88 (1) |
| 13 | 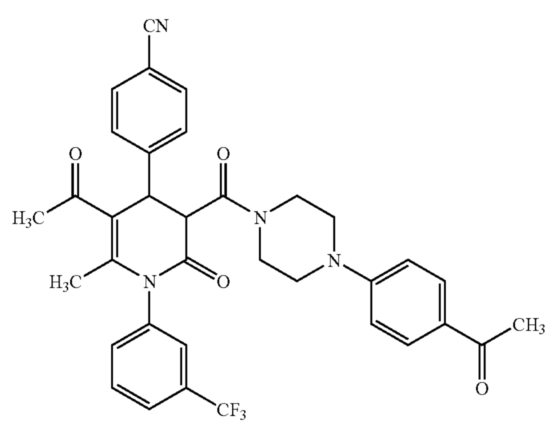 | 28 | 630 | 2.61 (1) |

-continued

| Example No. | Structure | Yield [%] | MS (ESIpos): m/z (M + H)+ | Retention time (method) |
|---|---|---|---|---|
| 14 | 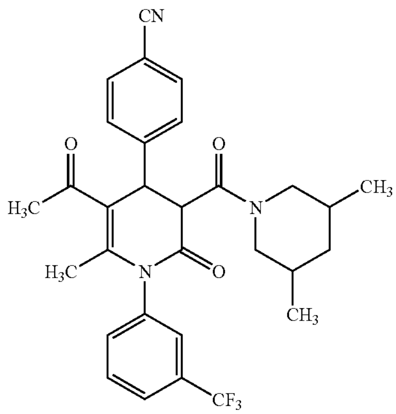 | 14 | 539 | 2.82 (1) |
| 15 | 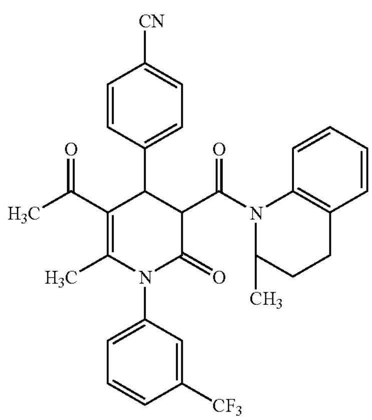 | 11 | 573 | 2.89 (1) |
| 16 | 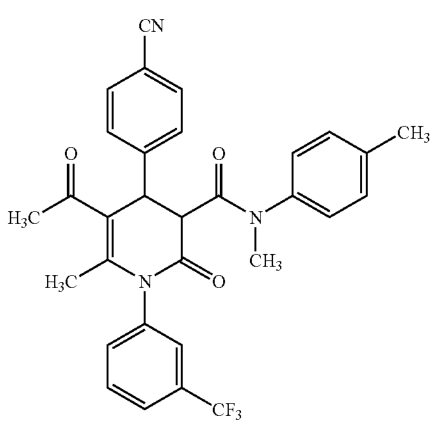 | 14 | 547 | 2.77 (1) |

| Example No. | Structure | Yield [%] | MS (ESIpos): m/z (M + H)+ | Retention time (method) |
|---|---|---|---|---|
| 17 | 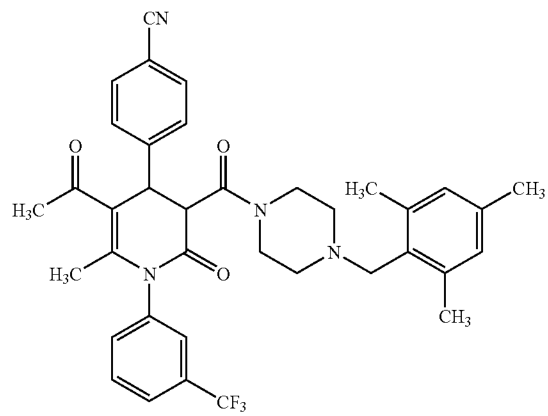 | 31 | 644 | 2.44 (1) |
| 18 | 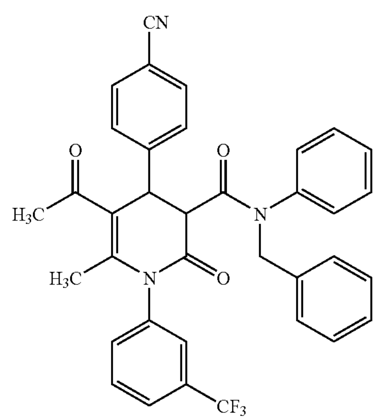 | 14 | 609 | 2.96 (1) |
| 19 | 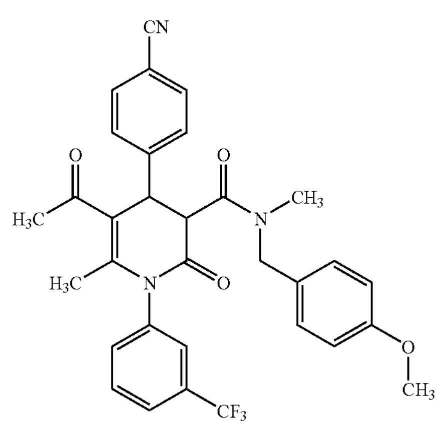 | 20 | 577 | 2.69 (1) |

-continued

| Example No. | Structure | Yield [%] | MS (ESIpos): m/z (M + H)+ | Retention time (method) |
|---|---|---|---|---|
| 20 | 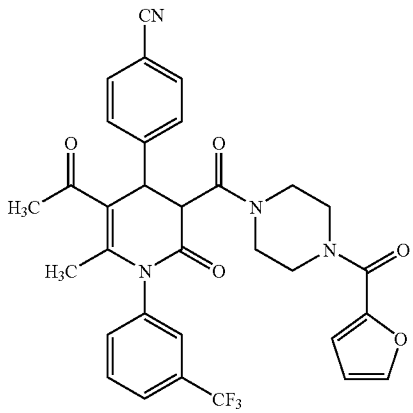 | 47 | 606 | 2.41 (1) |
| 21 | 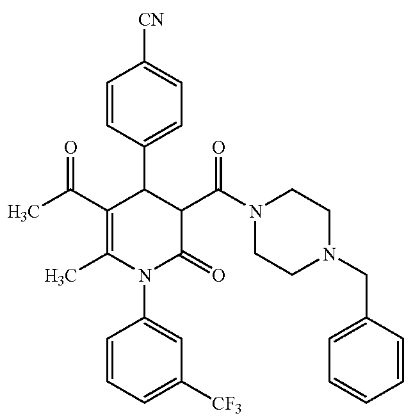 | 20 | 602 | 2.16 (1) |
| 22 | 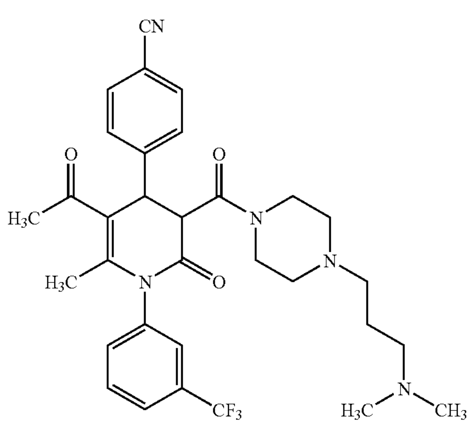 | 39 | 597 | 1.67 (1) |

-continued

| Example No. | Structure | Yield [%] | MS (ESIpos): m/z (M + H)+ | Retention time (method) |
|---|---|---|---|---|
| 23 | 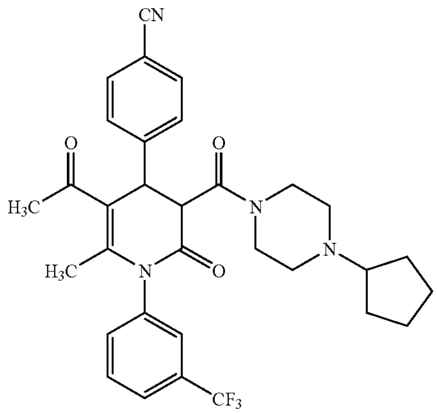 | 21 | 580 | 2.05 (1) |
| 24 | 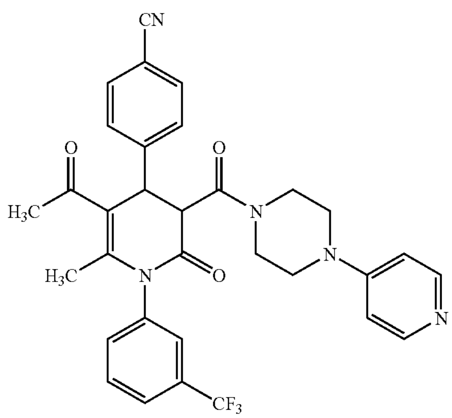 | 39 | 589 | 1.95 (1) |
| 25 | 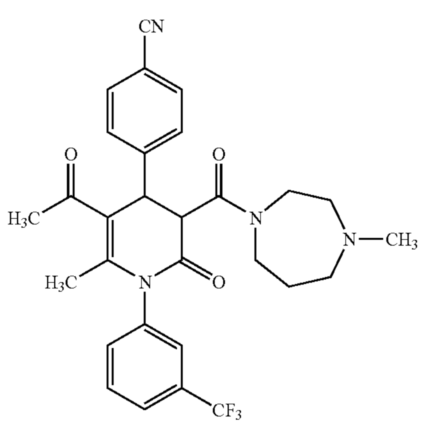 | 27 | 540 | 1.88 (1) |

-continued

| Example No. | Structure | Yield [%] | MS (ESIpos): m/z (M + H)$^+$ | Retention time (method) |
|---|---|---|---|---|
| 26 | 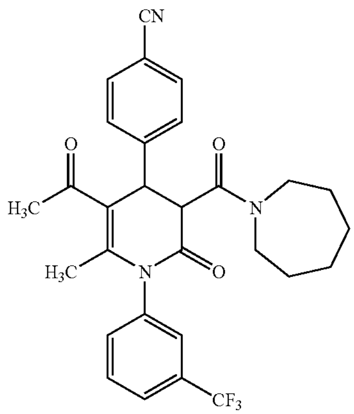 | 22 | 525 | 2.62 (1) |
| 27 | 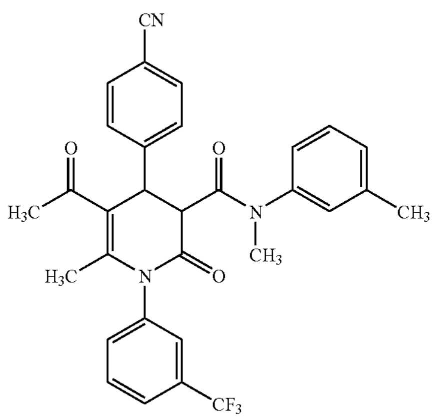 | 31 | 547 | 2.76 (1) |
| 28 | 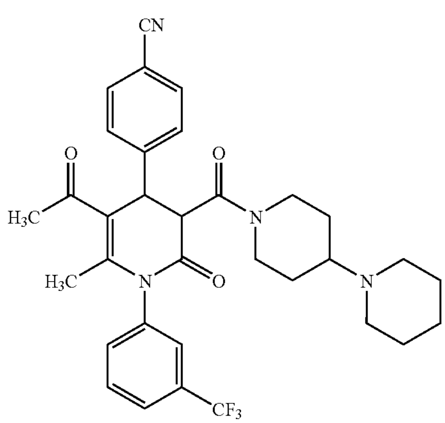 | 10 | 594 | 1.97 (1) |

-continued

| Example No. | Structure | Yield [%] | MS (ESIpos): m/z (M + H)+ | Retention time (method) |
|---|---|---|---|---|
| 29 | 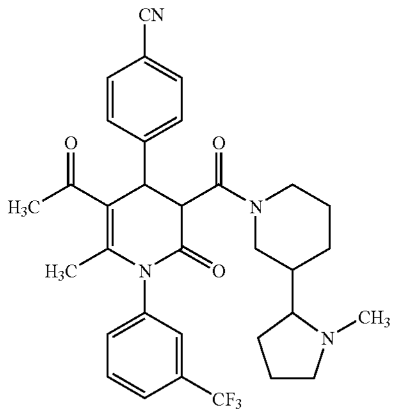 | 11 | 594 | 1.99 (1) |
| 30 | 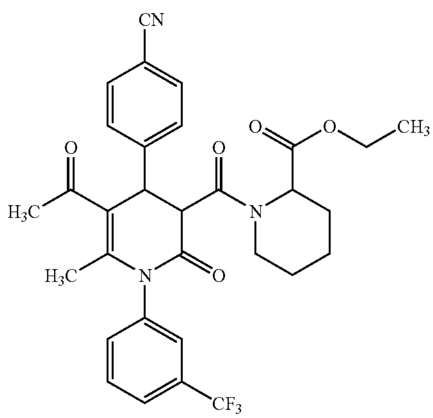 | 31 | 583 | 2.77 (1) |
| 31 | 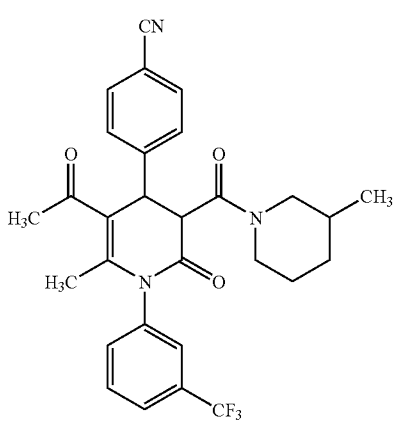 | 21 | 525 | 2.69 (1) |

-continued

| Example No. | Structure | Yield [%] | MS (ESIpos): m/z (M + H)+ | Retention time (method) |
|---|---|---|---|---|
| 32 | 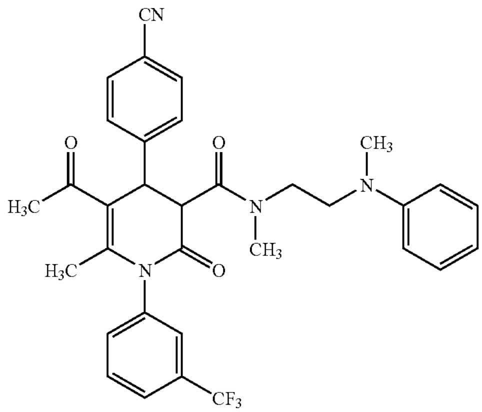 | 31 | 590 | 2.79 (1) |
| 33 | 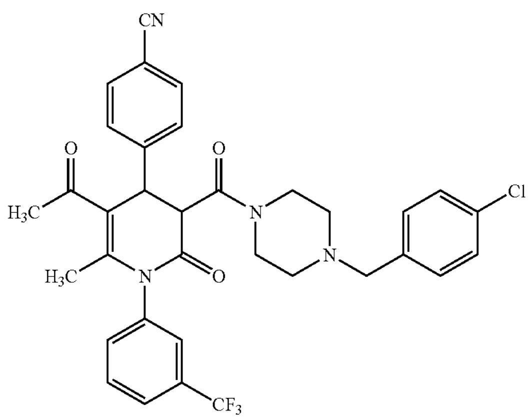 | 26 | 636 | 2.3 (1) |
| 34 | 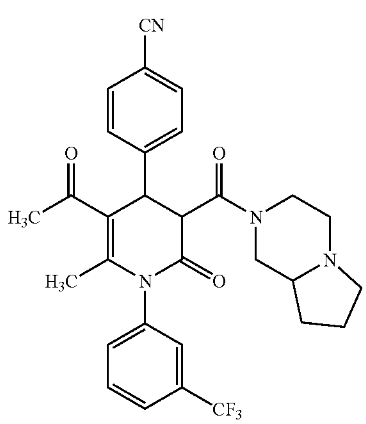 | 22 | 552 | 1.93 (1) |

-continued

| Example No. | Structure | Yield [%] | MS (ESIpos): m/z (M + H)+ | Retention time (method) |
|---|---|---|---|---|
| 35 | (structure) | 7 | 539 | 2.78 (1) |
| 36 | (structure) | 47 | 524 | 2.45 (1) |
| 37 | (structure) | 9 | 608 | 2.16 (1) |

-continued
| Example No. | Structure | Yield [%] | MS (ESIpos): m/z (M + H)+ | Retention time (method) |
|---|---|---|---|---|
| 38 | 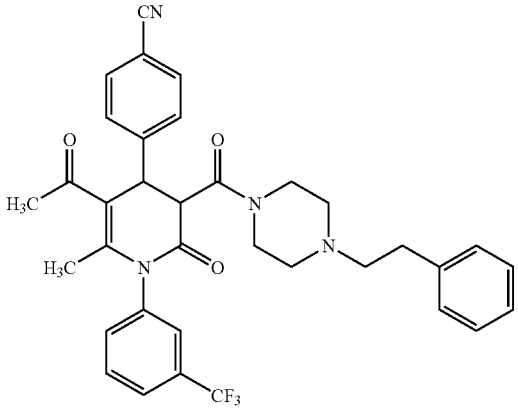 | 27 | 616 | 2.23 (1) |
| 39 | 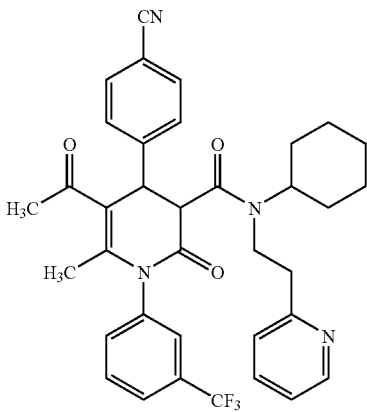 | 42 | 630 | 2.44 (1) |
| 40 | 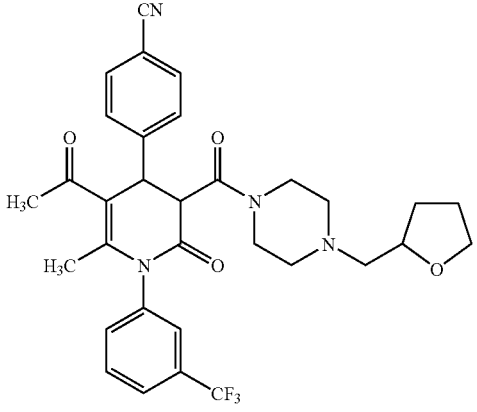 | 21 | 596 | 2.0 (1) |

-continued
| Example No. | Structure | Yield [%] | MS (ESIpos): m/z (M + H)+ | Retention time (method) |
|---|---|---|---|---|
| 41 | 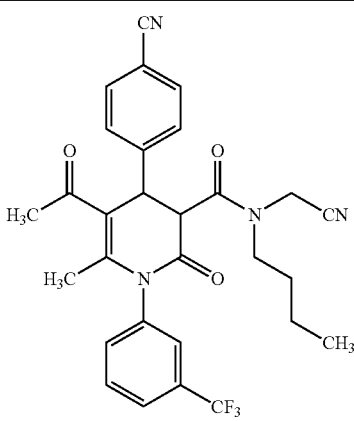 | 29 | 538 | 2.67 (1) |
| 42 | 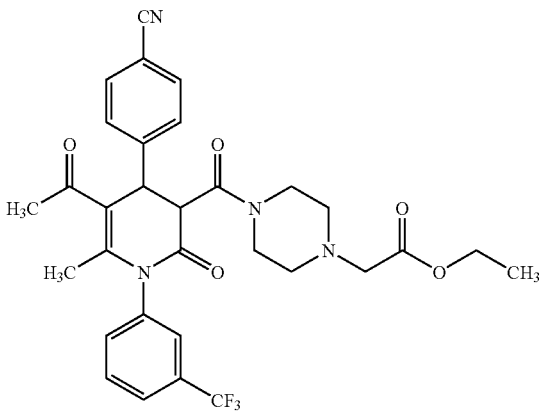 | 13 | 598 | 2.24 (1) |
| 43 | 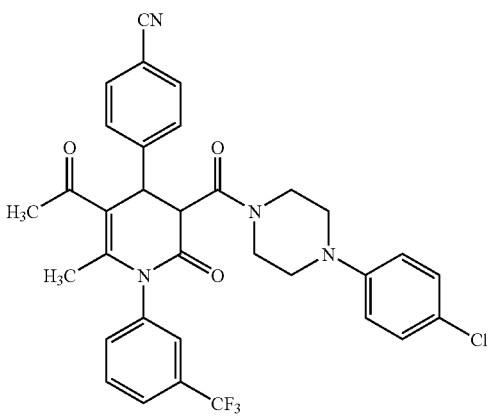 | 82 | 622 | 2.91 (1) |

-continued

| Example No. | Structure | Yield [%] | MS (ESIpos): m/z (M + H)⁺ | Retention time (method) |
|---|---|---|---|---|
| 44 | 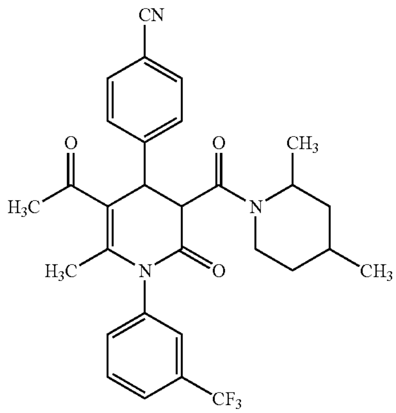 | 12 | 539 | 2.76 (1) |
| 45 | 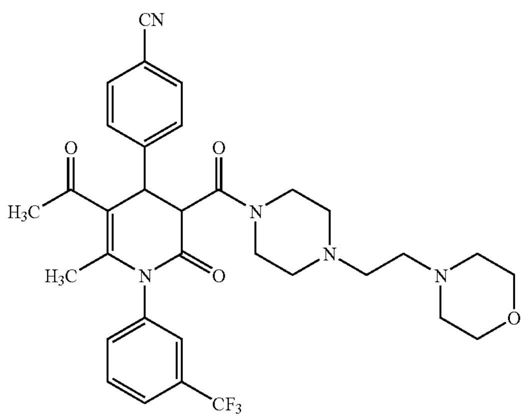 | 19 | 625 | 1.9 (1) |
| 46 | 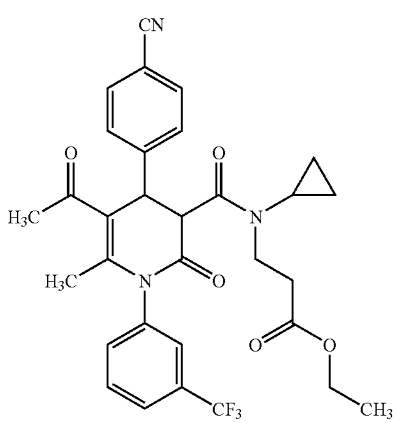 | 22 | 583 | 2.67 (1) |

-continued

| Example No. | Structure | Yield [%] | MS (ESIpos): m/z (M + H)+ | Retention time (method) |
|---|---|---|---|---|
| 47 | 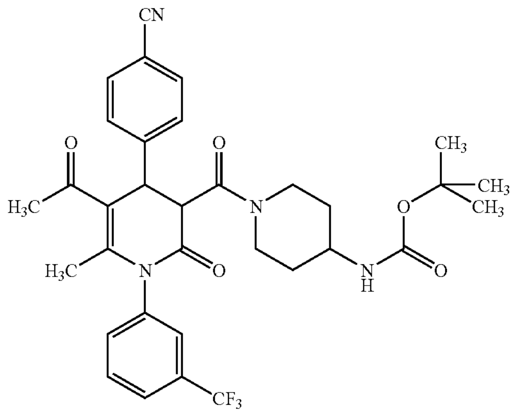 | 6 | 626 | 2.65 (1) |
| 48 | 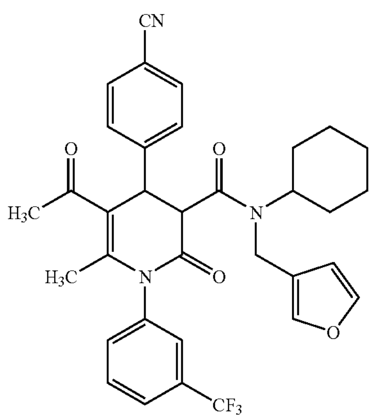 | 18 | 605 | 2.98 (1) |
| 49 | 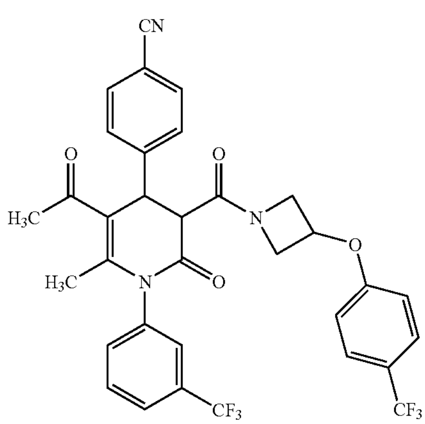 | 24 | 643 | 2.91 (1) |

-continued

| Example No. | Structure | Yield [%] | MS (ESIpos): m/z (M + H)+ | Retention time (method) |
|---|---|---|---|---|
| 50 | 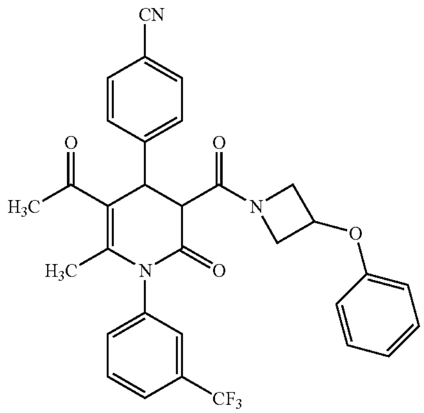 | 10 | 575 | 2.74 (1) |
| 51 | 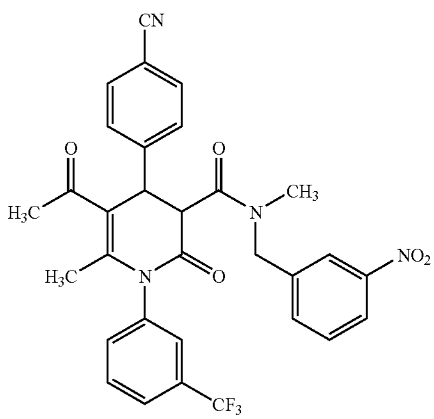 | 17 | 592 | 2.27 (2) |
| 52 | 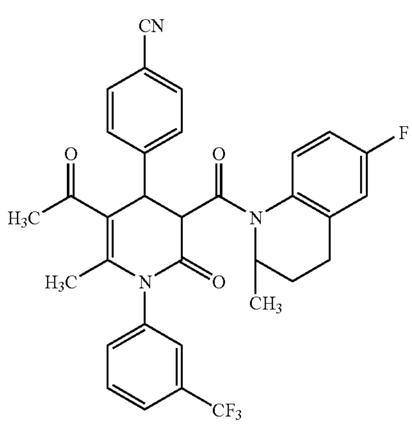 | 10 | 591 | 2.4 (2) |

-continued

| Example No. | Structure | Yield [%] | MS (ESIpos): m/z (M + H)+ | Retention time (method) |
|---|---|---|---|---|
| 53 | 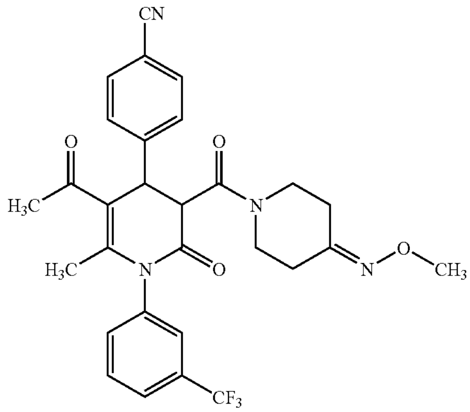 | 46 | 554 | 2.14 (2) |
| 54 | 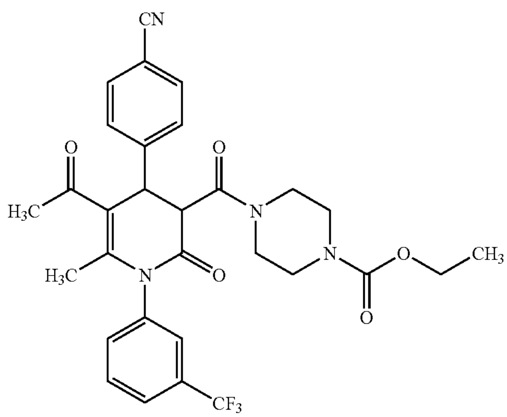 | 47 | 584 | 2.14 (2) |
| 55 | 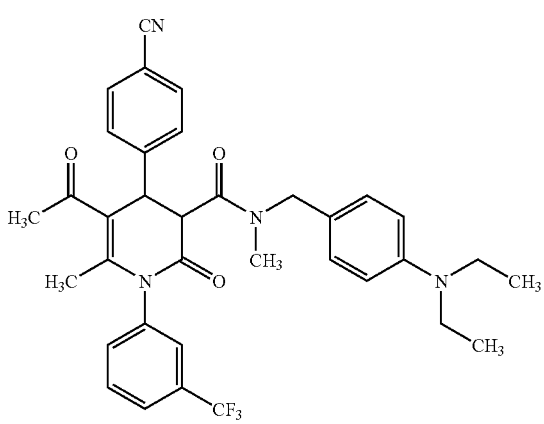 | 9 | 618 | 1.75 (2) |

-continued

| Example No. | Structure | Yield [%] | MS (ESIpos): m/z (M + H)+ | Retention time (method) |
|---|---|---|---|---|
| 56 | 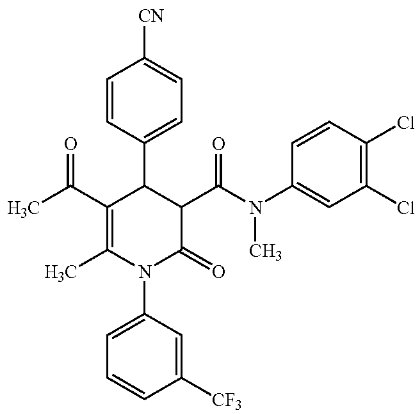 | 12 | 601 | 2.41 (2) |
| 57 | 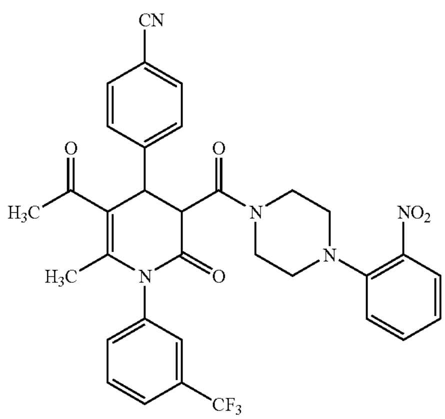 | 33 | 633 | 2.32 (2) |
| 58 | 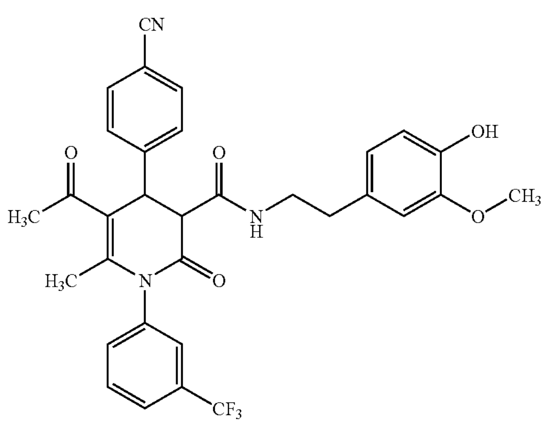 | 32 | 593 | 2.11 (2) |

-continued

| Example No. | Structure | Yield [%] | MS (ESIpos): m/z (M + H)+ | Retention time (method) |
|---|---|---|---|---|
| 59 | 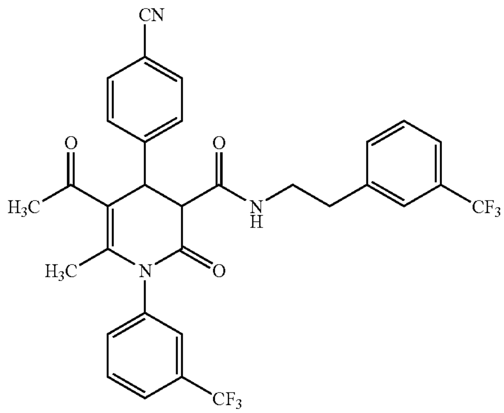 | 17 | 615 | 2.38 (2) |
| 60 | 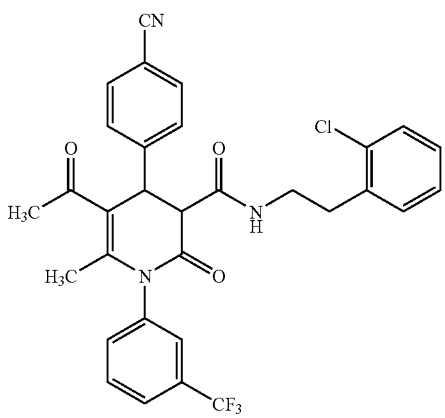 | 18 | 581 | 2.35 (2) |
| 61 | 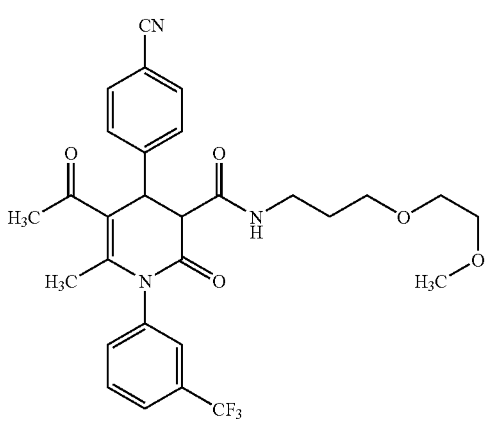 | 38 | 559 | 2.04 (2) |

-continued

| Example No. | Structure | Yield [%] | MS (ESIpos): m/z (M + H)+ | Retention time (method) |
|---|---|---|---|---|
| 62 | 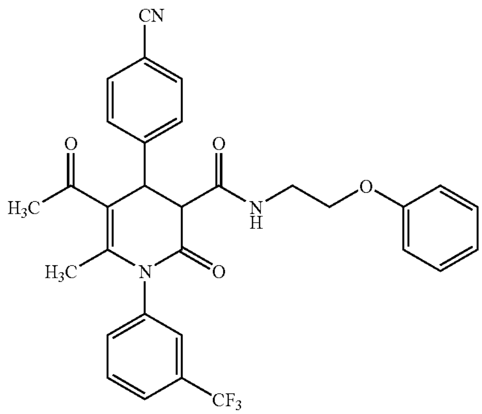 | 21 | 563 | 2.27 (2) |
| 63 | 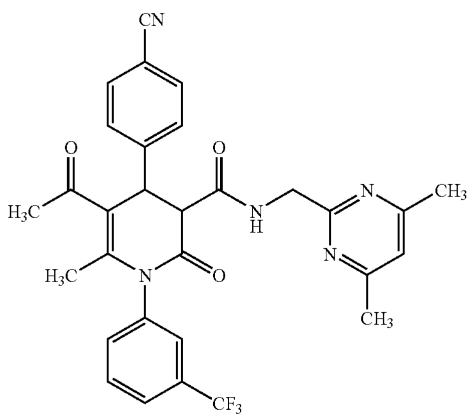 | 46 | 563 | 2.06 (2) |
| 64 | 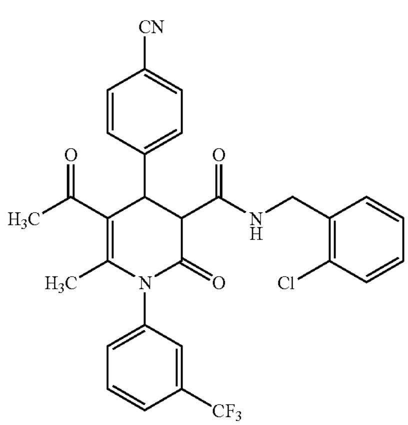 | 18 | 567 | 2.31 (2) |

-continued

| Example No. | Structure | Yield [%] | MS (ESIpos): m/z (M + H)+ | Retention time (method) |
|---|---|---|---|---|
| 65 | 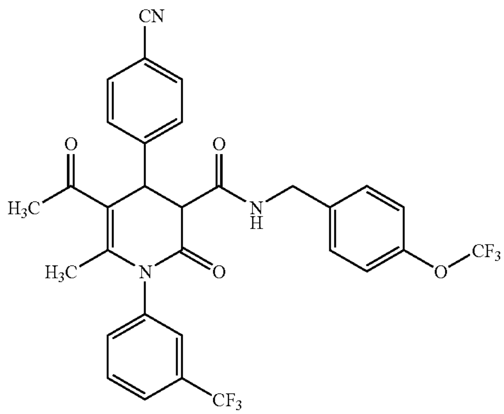 | 19 | 617 | 2.37 (2) |
| 66 | 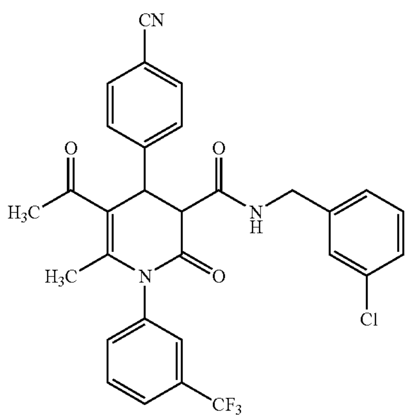 | 17 | 567 | 2.3 (2) |
| 67 | 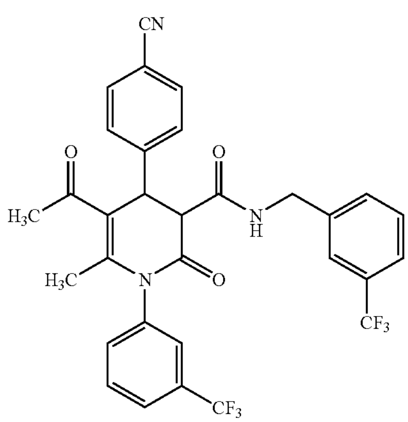 | 17 | 601 | 2.34 (2) |

-continued

| Example No. | Structure | Yield [%] | MS (ESIpos): m/z (M + H)+ | Retention time (method) |
|---|---|---|---|---|
| 68 | 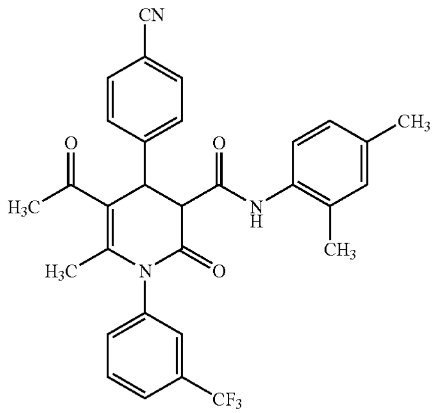 | 25 | 547 | 2.34 (2) |
| 69 | 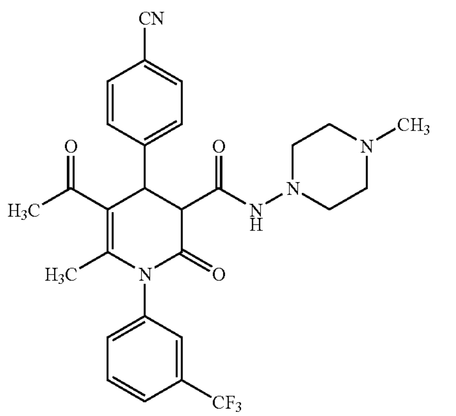 | 27 | 541 | 1.49 (2) |
| 70 | 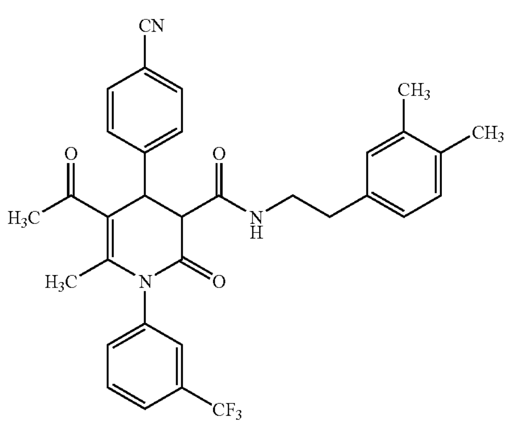 | 11 | 575 | 2.4 (2) |

-continued

| Example No. | Structure | Yield [%] | MS (ESIpos): m/z (M + H)+ | Retention time (method) |
|---|---|---|---|---|
| 71 | 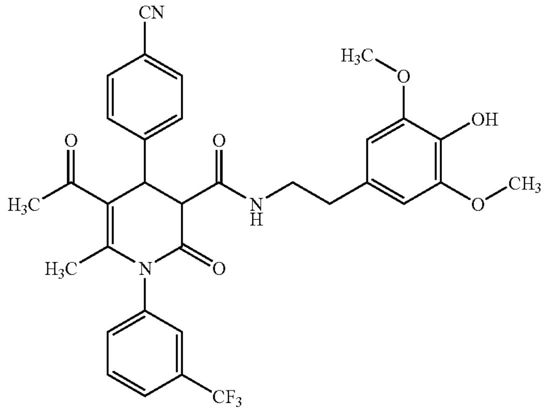 | 35 | 623 | 2.08 (2) |
| 72 | 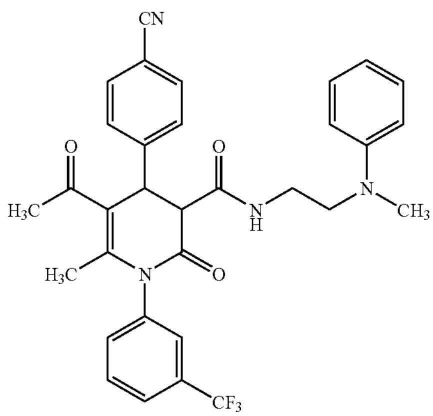 | 16 | 576 | 2.3 (2) |
| 73 | 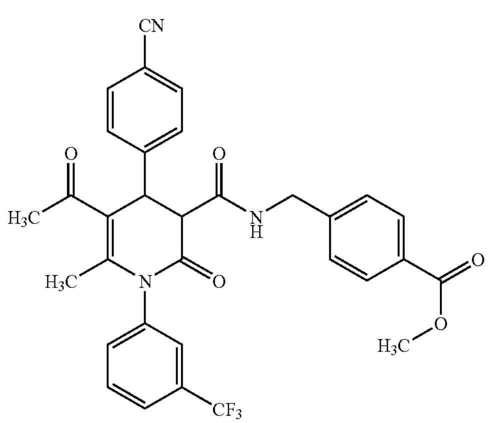 | 19 | 591 | 2.2 (2) |

-continued

| Example No. | Structure | Yield [%] | MS (ESIpos): m/z (M + H)$^+$ | Retention time (method) |
|---|---|---|---|---|
| 74 | 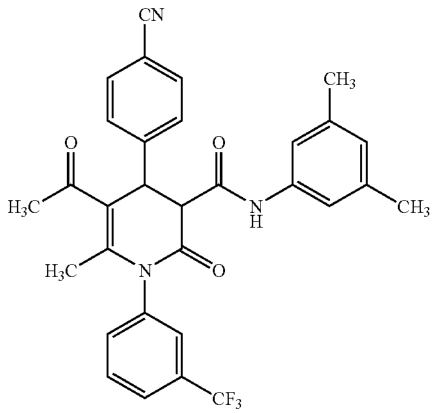 | 30 | 547 | 2.39 (2) |
| 75 | 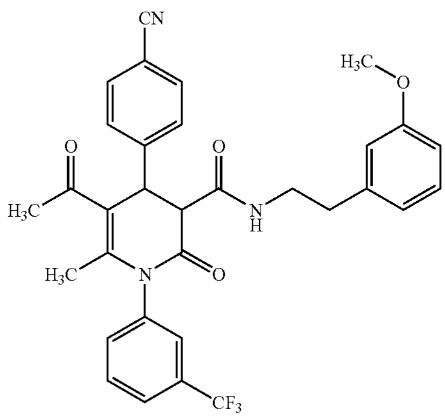 | 5 | 577 | 2.27 (2) |
| 76 | 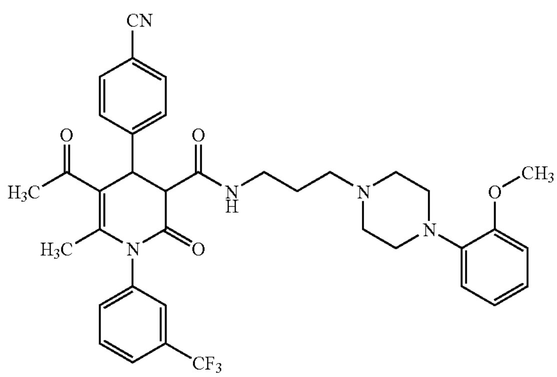 | 6 | 675 | 1.67 (2) |

C. Operative Examples Relating to Pharmaceutical Compositions

The compounds according to the invention can be converted into pharmaceutical preparations as follows:

Tablet:
Composition:

100 mg of the compound of Example 1, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, curvature radius 12 mm.

Preparation:

The mixture of active component, lactose and starch is granulated with a 5% solution (m/m) of the PVP in water. After drying, the granules are mixed with magnesium stearate for 5 min. This mixture is moulded using a customary tablet press (tablet format, see above). The moulding force applied is typically 15 kN.

Orally Administrable Suspension:
Composition:

1000 mg of the compound of Example 1, 1000 mg of ethanol (96%), 400 mg of Rhodigel (xanthan gum from FMC, Pennsylvania, USA) and 99 g of water.

A single dose of 100 mg of the compound according to the invention is provided by 10 ml of oral suspension.

Preparation:

The Rhodigel is suspended in ethanol and the active component is added to the suspension. The water is added with stirring. Stirring is continued for about 6 h until the swelling of the Rhodigel is complete.

We claim:

1. A compound of formula (I)

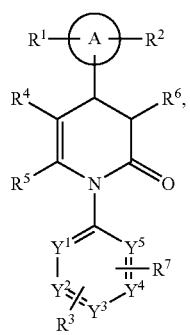

wherein
A represents a phenyl ring,
$R^1$ represents hydrogen,
$R^2$ represents cyano, bromo or nitro,
$R^3$ represents hydrogen,
$R^4$ represents $C_1$-$C_4$-alkylcarbonyl, $C_1$-$C_4$-alkoxycarbonyl or cyano, wherein $C_1$-$C_4$-alkylcarbonyl and $C_1$-$C_4$-alkoxycarbonyl can be substituted with hydroxycarbonyl or $C_1$-$C_4$-alkoxycarbonyl,
$R^5$ represents methyl,
$R^6$ represents a group of the formula

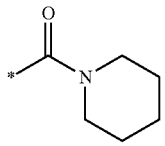

which is substituted by one or two radicals independently selected from the group consisting of $C_1$-$C_4$-alkyl, hydroxy, $C_1$-$C_4$-alkoxy, hydroxycarbonyl, $C_1$-$C_4$-alkoxycarbonyl, $C_1$-$C_4$-alkoxycarbonylamino, oxo, pyrrolidino, piperidino and morpholino, or
$R^6$ represents a group of the formula

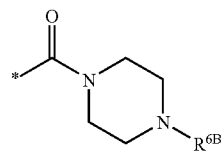

wherein $R^{6B}$ is selected from the group consisting of: phenyl or pyridyl each of which can be further substituted by up to three radicals independently selected from the group consisting of fluoro, chloro, trifluoromethyl, nitro, cyano, $C_1$-$C_4$-alkyl, hydroxycarbonyl, $C_1$-$C_4$-alkoxycarbonyl and $C_1$-$C_4$-alkylcarbonyl; $C_1$-$C_4$-alkyl which is substituted by hydroxy, $C_1$-$C_4$-alkoxy, di-$C_1$-$C_4$-alkylamino, hydroxycarbonyl, $C_1$-$C_4$-alkoxycarbonyl, tetrahydrofuryl, morpholinyl, thienyl or by phenyl which for its part can be further substituted by up to three radicals independently selected from the group consisting of $C_1$-$C_4$-alkyl, fluoro, chloro and hydroxycarbonyl; and $C_1$-$C_4$-alkoxycarbonyl, or $R^6$ represents mono- or di-$C_1$-$C_4$-alkylaminocarbonyl wherein the alkyl moiety or at least one alkyl moiety, respectively, is substituted by: phenyl, pyridyl or pyrimidinyl each of which are further substituted by one, two or three radicals independently selected from the group consisting of fluoro, chloro, nitro, cyano, trifluoromethyl, $C_1$-$C_4$-alkyl, hydroxy, $C_1$-$C_4$-alkoxy, trifluoromethoxy, di-$C_1$-$C_4$-alkylamino, hydroxycarbonyl and $C_1$-$C_4$-alkoxycarbonyl; $C_1$-$C_4$-alkoxy which is further substituted by hydroxy, $C_1$-$C_4$-alkoxy, di-$C_1$-$C_4$-alkylamino, $C_1$-$C_4$-alkoxycarbonyl or hydroxycarbonyl; or by a group of the formula

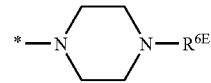

wherein $R^{6E}$ represents $C_1$-$C_4$-alkyl, $C_1$-$C_4$-alkylcarbonyl, $C_1$-$C_4$-alkoxycarbonyl or phenyl which for its part can be further substituted by fluoro, chloro, $C_1$-$C_4$-alkyl or $C_1$-$C_4$-alkoxy, or $R^6$ represents N—$C_1$-$C_4$-alkyl-N—$C_3$-$C_6$-cycloalkylaminocarbonyl wherein the alkyl moiety can be further substituted by phenyl, furyl, pyridyl, hydroxycarbonyl or $C_1$-$C_4$-alkoxycarbonyl, $R^7$ represents trifluoromethyl or nitro,
and
$Y^1, Y^2, Y^3, Y^4$ and $Y^5$ each represent CH.

2. A compound according to claim 1, wherein $R^2$ is cyano, and $R^4$ is acetyl, methoxycarbonyl, ethoxycarbonyl or cyano.

3. A pharmaceutical composition comprising a pharmacologically acceptable excipient and the compound of claim 1 or a tautomer or pharmaceutically acceptable salt thereof.

4. A method of controlling chronic obstructive pulmonary disease, acute coronary syndrome, acute myocardial infarction, or development of heart failure in a human or animal comprising the step of administering to a human or animal the compound of claim 1 or a tautomer or pharmaceutically acceptable salt thereof.

* * * * *